United States Patent
Löhr et al.

(10) Patent No.: US 8,252,925 B2
(45) Date of Patent: Aug. 28, 2012

(54) METHOD FOR THE PRODUCTION OF 3-PHENYL(THIO)URACILS AND DITHIOURACILS

(75) Inventors: Sandra Löhr, Ludwigshafen (DE); Joachim Gebhardt, Wachenheim (DE); Guido Mayer, Gönnheim (DE); Michael Keil, Freinsheim (DE); Thomas Schmidt, Neustadt (DE); Bernd Wolf, Fußgönheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1573 days.

(21) Appl. No.: 11/631,972

(22) PCT Filed: Jul. 13, 2005

(86) PCT No.: PCT/EP2005/007577
§ 371 (c)(1),
(2), (4) Date: Jan. 9, 2007

(87) PCT Pub. No.: WO2006/010474
PCT Pub. Date: Feb. 2, 2006

(65) Prior Publication Data
US 2008/0033174 A1    Feb. 7, 2008

(30) Foreign Application Priority Data
Jul. 22, 2004   (DE) .......................... 10 2004 035 656

(51) Int. Cl.
C07D 239/00     (2006.01)
C07D 239/02     (2006.01)
(52) U.S. Cl. ....................................................... 544/242
(58) Field of Classification Search ................... 544/242
See application file for complete search history.

(56) References Cited

U.S. PATENT DOCUMENTS

| | | | |
|---|---|---|---|
| 5,017,211 A | 5/1991 | Wenger et al. | |
| 6,130,225 A | 10/2000 | Drewes et al. | |
| 2005/0159622 A1 | 7/2005 | Hamprecht et al. | |

FOREIGN PATENT DOCUMENTS

| | | | |
|---|---|---|---|
| CA | 2 312 703 A1 | 6/1999 | |
| CA | 2 504 410 A1 | 5/2004 | |
| WO | WO 89/02891 A | 4/1989 | |
| WO | WO 98/06706 A | 2/1998 | |
| WO | WO 01/83459 A | 11/2001 | |
| WO | WO 01/83459 A2 | 11/2001 | |
| WO | WO 03/097589 A | 11/2003 | |
| WO | WO 2004/039768 A | 5/2004 | |
| WO | WO 2004/056785 A2 | 7/2004 | |

OTHER PUBLICATIONS

Houben-Weyl, Methoden der organischen Chemie, E5, (1985), pp. 972-981.
Houben-Weyl, Methoden der organischen Chemie, p. 655, (1952).
Houben-Weyl, Methoden der organischen Chemie, p. 10, (1958).
Press et al., "Synthesis of 5,6-Dimethoxyquinazolin-2(1H)-ones", J. Het. Chem., 23, 6, 1986, pp. 1821-1828.
Vauthey et al., "An environmentally benign access to carbamates and ureas", Tetrahedron Letters, 41 (2000), pp. 6347-6350.
Belley et al., "Synthesis of N-Aminoindole Ureas from Ethyl 1-Amino-6-(trifluoromethyl)-1H-indole-3-carboxylate", Synlett, 2, 2001, pp. 222-225.
Lutz et al., "Novel 6-(Trifluoromethyl)cytosines and 6-(Trifluoromethyl)uracils", J. of Heterocyclic Chem, 1972, 9, 3, pp. 513-522.
Sowada, Über die Alkylierung 1,3-disubstituierter Schwefelsäurediamide, J. Prakt. Chem., 25, (1964), pp. 88-94.
Unterhalt et al., "Trialkyl-und Tetraalkylsulfonyldiamide", Arch. Pharm., 314, pp. 51-57, (1981).
Bancroft, "Synthesis and Reduction of some 1H-2,1,3-Benzothiadiazin-4(3H)one 2, 2-Dioxides", J. Heterocycl., Chem., 15, (1978), pp. 1521-1523.
Houben-Weyl, Methoden der organishcne Chemie, E4, 1983, pp. 6-17.
Buehler et al., "Survey of Organic Syntheses", Interscience Publishers 1970, pp. 392-409.
Martinez et al., "Chiorophenylmethyl Benzothiadiazine Dioxides Derivatives: Potent Human Cytomegalovirus Inhibitors", Bioorganic & Medicinal Chemistry Letters 9, (1999), pp. 3133-3136.

*Primary Examiner* — Paul V. Ward
(74) *Attorney, Agent, or Firm* — Rothwell, Figg, Ernst & Manbeck, P.C.

(57) ABSTRACT

The present invention relates to a process for preparing 3-phenyl(thio)uracils and -dithiouracils of the formula I

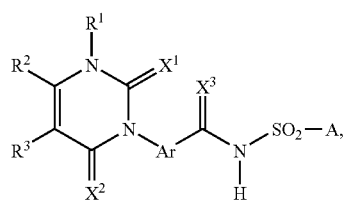

where the variables are each as defined in the description, and also intermediates for their preparation.

15 Claims, No Drawings

METHOD FOR THE PRODUCTION OF 3-PHENYL(THIO)URACILS AND DITHIOURACILS

CROSS REFERENCE TO RELATED APPLICATION

This application is a 35 USC §371 National Phase Entry Application from PCT/EP2005/007577, filed Jul. 13, 2005, and designating the United States.

The present invention relates to a process for preparing 3-phenyl(thio)uracils and -dithiouracils of the formula I

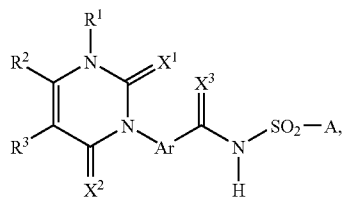

where the variables are each defined as follows:

$R^1$ is hydrogen, $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl, phenyl-$C_1$-$C_4$-alkyl or amino, $R^2$ and $R^3$ are each independently
hydrogen, $C_1$-$C_6$-alkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl or $C_3$-$C_6$-haloalkynyl;

$X^1$, $X^2$ and $X^3$ are each independently
oxygen or sulfur;

Ar is phenyl which may be partly or fully halogenated and/or may carry from one to three radicals from the group of cyano, $C_1$-$C_4$-alkyl or $C_1$-$C_4$-haloalkyl, and A is a radical derived from a primary or secondary amine or $NH_2$.

Phenyluracils which carry, in the meta-position to the uracil ring on the phenyl ring, a heterocycle or an unsaturated ester, thioester or amide radical which is attached to the phenyl ring via an oxygen or sulfur atom are known from WO 04/056785.

3-Phenyluracils of the general formula I and the corresponding thio- and dithiouracils are known in principle from WO 01/83459.

They are prepared in accordance with the teaching given in WO 01/83459 by the following methods A to C.

In the following schemes A to C, the variables Ar and A each have the definitions specified above among others, Hal is halogen and Q is an optionally substituted heterocycle:

Method A:

Condensation of a substituted benzoic acid with a substituted sulfuric diamide in the presence of N,N-carbonyldiimidazole (CDI) or conversion of the carboxylic acid to its acid chloride and subsequent reaction of the acid chloride with a sulfuric diamide according to the following scheme A:

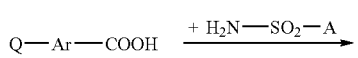

-continued

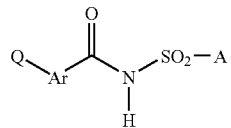

A disadvantage of this procedure is that the benzoic acid used is only obtainable from the precursor ester by cleavage using boron tribromide with corresponding salt formation. In addition, the yield of the condensation with sulfuric diamides is only between 16 and 45%. The detour via an acid chloride prepared beforehand also leads in only 26% yield to the desired benzoylsulfuric diamide.

Method B:

Replacement of a halogen atom with a uracil, thiouracil or dithiouracil radical according to the following scheme B:

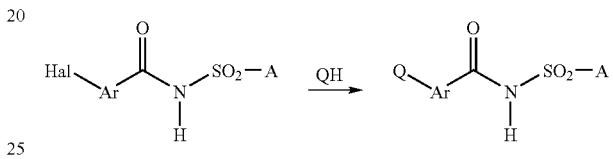

The method B has the disadvantage that the haloaromatic used first has to be prepared in a complicated manner by a Sandmeyer reaction. In addition, the selectivity of the reaction with respect to the halogen radical is unsatisfactory when further halogen substituents are present on Ar.

Method C:

Reaction of aniline compound with an oxazinone and subsequent alkylation of the resulting 3-phenyluracil in the presence of a base according to the following scheme C:

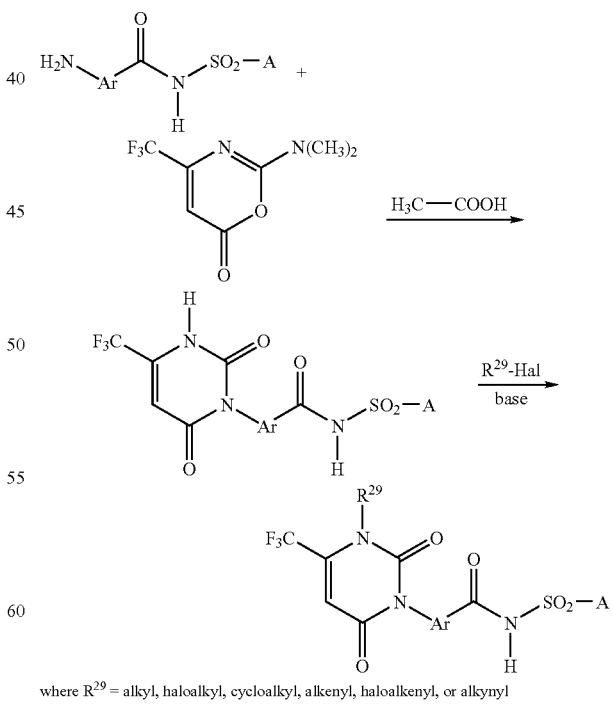

where $R^{29}$ = alkyl, haloalkyl, cycloalkyl, alkenyl, haloalkenyl, or alkynyl

It is disadvantageous that the oxazinone used first has to be prepared in a complicated manner by reacting an aminocrotonic ester with a dialkylcarbamoyl chloride and subsequently cyclizing with phosphorus oxychloride, phosphorus pentachloride or oxalyl chloride. This process is likewise not sufficiently economically viable owing to the starting materials used and the reaction stages.

It is therefore an object of the present invention to provide a process for preparing 3-phenyl(thio)uracils and -dithiouracils of the formula I which affords the 3-phenyl(thio)uracils and -dithiouracils of the formula I in high yields and good purity, and additionally overcomes the outlined disadvantages of the prior art.

It is a further object of the present invention to provide a simple and easy-to-handle process for preparing carbamates of the formula II, which affords the carbamates of the formula II in high yields and good purity.

It is a further object of the present invention to provide a process for preparing 3-phenyl(thio)uracils and -dithiouracils of the formula I, which additionally comprises the process for preparing the carbamates of the formula II.

It has been found that, surprisingly, this object is achieved by a process in which the carbamates of the formula II

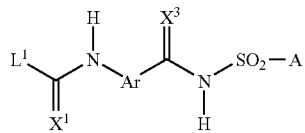

II where the variables $X^1$, $X^3$, Ar and A are each as defined above and $L^1$ is a nucleophilically displaceable leaving group; are reacted with enamines of the formula III

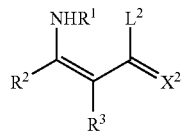

III where the variables $X^2$, $R^1$, $R^2$ and $R^3$ are each as defined above and $L^2$ is a nucleophilically displaceable leaving group.

The present invention therefore provides a process for preparing the above-defined 3-phenyl(thio)uracils and -dithiouracils of the formula I, comprising the reaction of carbamates of the formula II with an enamine of the formula III.

The carbamates of the formula II may themselves be prepared in analogy to the prior art processes (for example Houben-Weyl, Methoden der organischen Chemie [Methods of organic chemistry], E5, 1985, p. 972-980, and also VIII, p. 655 and XI part 2, p. 10; J. B. Press et al, J. Het. Chem., 23, 6, 1986, p. 1821-1828; I. Vanthey et al., Tetrahedron Lett. 41, 33, 2000, p. 6347-6350; M. Belley et al., Synlett, 2, 2001, p. 222-225) from amines of the formula IV

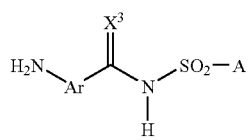

IV where $X^3$, Ar and A are each as defined above by reacting with a compound of the formula V

V where $X^1$ and $L^1$ are each as defined above and $L^3$ is a nucleophilically displaceable leaving group.

Accordingly the process according to the invention preferably comprises the provision of the carbamates of the formula II by this route.

The carbamates of the formula II are novel and likewise form part of the subject matter of the present invention as starting materials or intermediates in the process according to the invention.

The organic molecular moieties specified in the definition of the substituents $R^1$-$R^3$, Ar and A or as radicals on phenyl rings constitute, like the definition halogen, collective terms for individual lists of the individual group members, the expression $C_n$-$C_m$ specifying the possible number of the carbon atoms in the molecular moiety. All hydrocarbon chains, i.e. all alkyl, haloalkyl, cyanoalkyl, cyanoalkoxy, alkoxy, haloalkoxy, alkylthio, alkylsulfinyl, alkylsulfonyl, dialkylamino, alkylcarbonyl, alkoxycarbonyl, alkylaminocarbonyl, dialkylaminocarbonyl, alkenyl, haloalkenyl, alkenyloxy, haloalkenyloxy, alkynyl, haloalkynyl, alkynyloxy, haloalkynyloxy, alkoxyalkoxy and alkylthioalkoxy moieties, may be straight-chain or branched. Unless stated otherwise, halogenated substituents carry preferably from one to five identical or different halogen atoms. The definition halogen is in each case fluorine, chlorine, bromine or iodine.

Examples of Definitions Include:
- $C_1$-$C_4$-alkyl: for example methyl, ethyl, n-propyl, 1-methylethyl, n-butyl, 1-methylpropyl, 2-methylpropyl and 1,1-dimethylethyl;
- $C_1$-$C_6$-alkyl: $C_1$-$C_4$-alkyl as specified above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-di-methylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;
- $C_1$-$C_4$-alkylcarbonyl: for example methylcarbonyl, ethylcarbonyl, propylcarbonyl, 1-methylethylcarbonyl, butylcarbonyl, 1-methylpropylcarbonyl, 2-methylpropyl-carbonyl or 1,1-dimethylethylcarbonyl;
- $C_3$-$C_8$-cycloalkyl and the cycloalkyl moieties of $C_3$-$C_8$-cycloalkoxy: for example cyclopropyl, cyclobutyl, cyclopentyl, cyclohexyl, cycloheptyl and cyclooctyl;
- $C_3$-$C_8$-cycloalkenyl: for example cyclopropen-1-yl, cyclopropen-2-yl, cyclobuten-1-yl, cyclobuten-2-yl, cyclopenten-1-yl, cyclopent-2-en-1-yl, cyclopent-2,4-dien-1-yl, cyclohexen-1-yl, cyclohex-2-en-1-yl, cyclohex-3-en-1-yl; cyclohepten-1-yl, cyclohept-2-en-1-yl, cyclohept-3-en-1-yl, cycloocten-1-yl, cyclooct-2-en-1-yl, cyclooct-3-en-1-yl, cyclooct-4-en-1-yl;
- 3- to 6-membered heterocyclyl: a saturated, partially unsaturated or aromatic 3-, 4-, 5- or 6-membered heterocyclic ring which comprises from one to four identical or different heteroatoms selected from the group of oxygen, sulfur, nitrogen or the $NR^6$ group (where $R^6$ is hydrogen, $C_1$-$C_6$-alkyl, $C_3$-$C_6$-alkenyl or $C_3$-$C_6$-alkynyl), may if appropriate have one or two carbonyl groups or thiocarbonyl groups as ring members and may be bonded via C or N:

for example 2-oxrianyl, 2-oxetanyl, 3-oxetanyl, 2-aziridinyl, 3-thiethanyl, 1-azetidinyl, 2-azetidinyl, for example tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

for example tetrahydropyrrol-1-yl, tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

for example 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydro-oxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta$4-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl;

for example 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl, 1,2,4-$\Delta^4$-oxadiazolin-2-yl, 1,2,4-$\Delta^2$-oxadiazolin-4-yl, 1,2,4-$\Delta^3$-oxadiazolin-2-yl, 1,3,4-$\Delta^2$-oxadiazolin-4-yl, 1,2,4-$\Delta^5$-thiadiazolin-2-yl, 1,2,4-$\Delta^3$-thiadiazolin-2-yl, 1,2,4-$\Delta^2$-thiadiazolin-4-yl, 1,3,4-$\Delta^2$-thiadiazolin-4-yl, 1,2,3-$\Delta^2$-triazolin-1-yl, 1,2,4-$\Delta^2$-triazolin-1-yl, 1,2,4-$\Delta^2$-triazolin-4-yl, 1,2,4-$\Delta^3$-triazolin-1-yl, 1,2,4-$\Delta^1$-triazolin-4-yl;

for example 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazol-2-yl, 1,2,3-triazol-4-yl, 1,2,4-triazol-3-yl, tetrazol-5-yl;

for example pyrrol-1-yl, pyrazol-1-yl, imidazol-1-yl, 1,2,3-triazol-1-yl, 1,2,4-triazol-1-yl, tetrazol-1-yl;

for example tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

for example piperidin-1-yl, hexahydropyrimidin-1-yl, hexahydropyrazin-1-yl, hexahydropyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl, tetrahydro-1,2-oxazin-2-yl;

for example 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydro-pyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydro-pyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydro-pyridazin-4-yl, 1,2,5,6-tetrahydropyridazin-5-yl, 1,2,5,6-tetrahydro-pyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

for example 1,2,3,4-tetrahydropyridin-1-yl, 1,2,5,6-tetrahydropyridin-1-yl, 1,4-dihydropyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl;

for example pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: $C_3$-$C_6$-alkenyl as specified above and also ethenyl, $C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as specified above and also ethynyl;

$C_1$-$C_4$-haloalkyl: a $C_1$-$C_4$-alkyl radical as specified above which is partly or fully substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$-$C_6$-haloalkyl: $C_1$-$C_4$-haloalkyl as specified above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_2$-$C_6$-haloalkenyl and also the haloalkenyl moieties of $C_2$-$C_6$-haloalkenyloxy: a $C_2$-$C_6$-alkenyl radical as specified above which is partly or fully substituted by fluorine, chlorine, bromine and/or iodine, for example 2-chlorovinyl, 2-chloroallyl, 3-chloroallyl, 2,3-dichloroallyl, 3,3-dichloroallyl, 2,3,3-trichloroallyl, 2,3-dichlorobut-2-enyl, 2-bromovinyl, 2-bromoallyl, 3-bromoallyl, 2,3-dibromoallyl, 3,3-dibromoallyl, 2,3,3-tribromoallyl or 2,3-dibromobut-2-enyl;

$C_3$-$C_6$-haloalkynyl and the haloalkynyl moieties of $C_3$-$C_6$-haloalkynyloxy: a $C_3$-$C_6$-alkynyl radical as specified above which is partly or fully substituted by fluorine, chlorine, bromine and/or iodine, for example 1,1-difluoroprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_1$-$C_6$-cyanoalkyl and the cyanoalkyl moieties of $C_1$-$C_6$-cyanoalkoxy: $C_1$-$C_4$-cyanoalkyl as specified above and also 5-cyanopentyl, 6-cyanohexyl;

$C_1$-$C_4$-alkoxy, for example methoxy, ethoxy, propoxy, 1-methylethoxy, butoxy, 1-methylpropoxy, 2-methylpropoxy and 1,1-dimethylethoxy;

$C_1$-$C_6$-alkoxy: $C_1$-$C_4$-alkoxy as specified above, and also, for example, pentoxy, 1-methylbutoxy, 2-methylbutoxy, 3-methoxybutoxy, 1,1-dimethylpropoxy, 1,2-di-methylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-tri-methylpropoxy, 1-ethyl-1-methylpropoxy and 1-ethyl-2-methylpropoxy;

$C_2$-$C_6$-alkenyloxy: for example ethen-1-yloxy, ethen-2-yloxy, prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethyl-prop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4- en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$-$C_6$-alkynyloxy: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy and 4-methylpent-2-yn-5-yloxy;

$C_1$-$C_4$-haloalkoxy: a $C_1$-$C_4$-alkoxy radical as specified above which is partly or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as specified above, and also, for example, 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_4$-alkoxy-$C_2$-$C_4$-alkoxy: $C_2$-$C_4$-alkoxy substituted by $C_1$-$C_4$-alkoxy as specified above, i.e., for example, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy)propoxy, 2-(1-methylethoxy)propoxy, 2-(butoxy)-propoxy, 2-(1-methylpropoxy)propoxy, 2-(2-methylpropoxy)propoxy, 2-(1,1-dimethylethoxy)propoxy, 3-(methoxy)propoxy, 3-(ethoxy)propoxy, 3-(propoxy)-propoxy, 3-(1-methylethoxy)propoxy, 3-(butoxy)propoxy, 3-(1-methylpropoxy)-propoxy, 3-(2-methylpropoxy)propoxy, 3-(1,1-dimethylethoxy)propoxy, 2-(methoxy)butoxy, 2-(ethoxy)butoxy, 2-(propoxy)butoxy, 2-(1-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy)butoxy, 3-(1-methylethoxy)butoxy, 3-(butoxy)butoxy, 3-(1-methylpropoxy)butoxy, 3-(2-methylpropoxy)butoxy, 3-(1,1-dimethylethoxy)butoxy, 4-(methoxy)butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy and 4-(1,1-dimethylethoxy)butoxy;

$C_1$-$C_4$-alkoxycarbonyl: for example, methoxycarbonyl, ethoxycarbonyl, propoxycarbonyl, 1-methylethoxycarbonyl, butoxycarbonyl, 1-methylpropoxy-carbonyl, 2-methylpropoxycarbonyl or 1,1-dimethylethoxycarbonyl;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as specified above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_4$-alkylsulfinyl ($C_1$-$C_4$-alkyl-S(=O)—): for example methylsulfinyl, ethylsulfinyl, propylsulfinyl, 1-methylethylsulfinyl, butylsulfinyl, 1-methylpropylsulfinyl, 2-methyl-propylsulfinyl, 1,1-dimethylethylsulfinyl;

$C_1$-$C_4$-alkylsulfonyl ($C_1$-$C_4$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl;

$C_1$-$C_4$-alkylamino: for example methylamino, ethylamino, propylamino, 1-methyl-ethylamino, butylamino, 1-methylpropylamino, 2-methylpropylamino, 1,1-dimethylethylamino; di-($C_1$-$C_4$-alkyl)amino: for example N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethyl-ethyl)amino, N-(1-methylethyl)-N-propylamino, N-butyl-N-propylamino, N-(1-methylpropyl)-N-propylamino, N-(2-methylpropyl)-N-propylamino, N-(1,1-dimethyl-ethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethyl-ethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

($C_1$-$C_4$-alkylamino)carbonyl: for example methylaminocarbonyl, ethylamino-carbonyl, propylaminocarbonyl, 1-methylethylaminocarbonyl, butylaminocarbonyl, 1-methylpropylaminocarbonyl, 2-methylpropylaminocarbonyl or 1,1-dimethylethyl-aminocarbonyl;

di-($C_1$-$C_4$)-alkylaminocarbonyl: for example N,N-dimethylaminocarbonyl, N,N-diethylaminocarbonyl, N,N-di-(1-methylethyl)aminocarbonyl, N,N-dipropylaminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methyl-propyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methyl-propyl)-N-propylaminocarbonyl, N-(1,1-dimethylethyl)-N-propylaminocarbonyl, N-butyl-N-(1-methylethyl)aminocarbonyl, N-(1-methylethyl)-N-(1-methylpropyl)amino-carbonyl, N-(1-methylethyl)-N-(2-methylpropyl)aminocarbonyl, N-(1,1-dimethyl-ethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)amino-carbonyl, N-(1-methylpropyl)-N-(2-methylpropyl)aminocarbonyl, N-(1,1-dimethylethyl)-N-(1-methylpropyl)aminocarbonyl or N-(1,1-dimethylethyl)-N-(2-methylpropyl)aminocarbonyl.

All phenyl rings are preferably unsubstituted or carry from one to three halogen atoms and/or one nitro group, one cyano radical and/or one or two methyl, trifluoromethyl, methoxy or trifluoromethoxy substituents.

In a particularly preferred embodiment of the process according to the invention, the variables $R^1$, $R^2$ and $R^3$, each alone or in combination, are defined as follows:

$R^1$ hydrogen, $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl,
  very preferably hydrogen or $C_1$-$C_4$-alkyl,
  more preferably hydrogen, methyl or ethyl,
  especially preferably methyl;
  likewise preferably hydrogen, amino or $C_1$-$C_4$-alkyl,
  more preferably hydrogen, amino, methyl or ethyl,
  especially preferably amino or methyl;
  likewise preferably hydrogen, amino or $C_1$-$C_4$-alkyl,
  more preferably hydrogen or amino,
  especially preferably hydrogen;

$R^2$ hydrogen, $C_1$-$C_4$-alkyl or $C_1$-$C_4$-haloalkyl,
  more preferably hydrogen, methyl, difluoromethyl or trifluoromethyl,
  especially preferably trifluoromethyl;

$R^3$ hydrogen or $C_1$-$C_4$-alkyl,
  more preferably hydrogen.

In a further preferred embodiment of the process according to the invention, $X^1$, $X^2$ and $X^3$ are each oxygen.

The Ar group specified is preferably a group of the general formula Ar-1

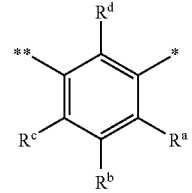

Ar-1 where
  * represents the bond of Ar to the $C(X^3)$ group;
    where X is preferably oxygen;
  ** represents the bond of Ar to the directly adjacent nitrogen atom; and
  $R^a$, $R^b$, $R^c$ and $R^d$ are each independently
    hydrogen, halogen, cyano or $C_1$-$C_4$-haloalkyl.

In a particularly preferred embodiment of the process according to the invention, the variables $R^a$, $R^b$, $R^c$ and $R^d$, each alone or in combination, are defined as follows:

$R^a$ hydrogen, halogen or cyano,
  especially preferably hydrogen, fluorine, chlorine or cyano,
  very preferably hydrogen, chlorine or cyano,
  exceptionally preferably hydrogen or chlorine;

$R^b$ hydrogen:

$R^c$ hydrogen or halogen,
  especially preferably hydrogen, fluorine or chlorine,
  very preferably hydrogen or fluorine,
  exceptionally preferably fluorine;

$R^d$ hydrogen.

The specified A radical derived from a primary or secondary amine is generally a group of the formula —$NR^4R^5$ where the variables $R^4$ and $R^5$ are each independently defined as follows:

$R^4$, $R^5$ hydrogen, $C_1$-$C_6$-alkyl, $C_2$-$C_6$-alkenyl or $C_2$-$C_6$-alkynyl,
  where the last three radicals mentioned may be substituted by a radical selected from the group of CN, $NO_2$, $C_1$-$C_4$-alkoxy, $C_1$-$C_4$-alkylthio, formyl, $C_1$-$C_4$-alkylcarbonyl, $C_1$-$C_4$-alkoxycarbonyl, ($C_1$-$C_4$-alkylamino)carbonyl, ($C_1$-$C_4$-dialkylamino)carbonyl, $C_1$-$C_4$-alkylsulfinyl, $C_1$-$C_4$-alkylsulfonyl, $C_3$-$C_8$-cycloalkyl, 3- to 6-membered heterocyclyl having from one to four heteroatoms selected from oxygen, sulfur, nitrogen and an $NR^6$ group,
    where $R^6$ is hydrogen, $C_1$-$C_6$-alkyl, $C_3$-$C_6$-alkenyl or $C_3$-$C_6$-alkynyl; or
  phenyl which may itself be partly or fully halogenated and/or may carry from one to three substituents selected from the group of cyano, nitro, $C_1$-$C_4$-alkyl, $C_1$-$C_4$- fluoroalkyl, $C_1$-$C_4$-alkoxy, ($C_1$-$C_4$-alkyl)amino, ($C_1$-$C_4$-dialkyl)amino, trifluoromethylsulfonyl, formyl or $C_1$-$C_4$-alkyloxycarbonyl;

$C_1$-$C_6$-haloalkyl, $C_2$-$C_6$-haloalkenyl, $C_3$-$C_6$-haloalkynyl;

$C_3$-$C_8$-cycloalkyl, $C_3$-$C_8$-cycloalkenyl, 3- to 6-membered heterocyclyl having from one to four heteroatoms selected from oxygen, sulfur, nitrogen and an $NR^6$ group, where $R^6$ is hydrogen, $C_1$-$C_6$-alkyl, $C_3$-$C_6$-alkenyl or $C_3$-$C_6$-alkynyl; phenyl or naphthyl;

where the last five radicals mentioned, $C_3$-$C_8$-cycloalkyl, $C_3$-$C_8$-cycloalkenyl, 3- to 6-membered heterocyclyl, phenyl and naphthyl, may themselves be partly or fully halogenated and/or may carry from one to three substituents selected from the group of cyano, nitro, $C_1$-$C_4$-alkyl, $C_1$-$C_4$-fluoroalkyl, $C_1$-$C_4$-alkoxy, ($C_1$-$C_4$-alkyl)amino, ($C_1$-$C_4$-dialkyl)amino, trifluoromethylsulfonyl, formyl, $C_1$-$C_4$-alkyloxycarbonyl or phenoxy; or $R^4$ and $R^5$ together form a saturated or partly unsaturated 5- to 6-membered nitrogen heterocycle which may have one or two carbonyl groups, thiocarbonyl groups and/or one or two further heteroatoms selected from O, S, N and an $NR^6$ group as ring members, where $R^6$ is hydrogen, $C_1$-$C_6$-alkyl, $C_3$-$C_6$-alkenyl or $C_3$-$C_6$-alkynyl, and which may itself be substituted by $C_1$-$C_4$-alkyl, $C_1$-$C_4$-alkoxy and/or $C_1$-$C_4$-haloalkyl.

For the process according to the invention, it has been found to be particularly advantageous when A is a group of the formula —$NR^4R^5$ where the substituents $R^4$ and $R^5$ are each independently hydrogen or $C_1$-$C_6$-alkyl which may itself be substituted by a substituent selected from the group of halogen, cyano, $C_3$-$C_8$-cycloalkyl, $C_1$-$C_4$-alkoxy, $C_1$-$C_4$-alkylthio, $C_1$-$C_4$-alkoxycarbonyl, phenyl which may itself carry from one to three radicals from the group of halogen or $C_1$-$C_4$-alkoxy;

furyl, thienyl and 1,3-dioxolanyl;

preferably halogen, cyano and $C_1$-$C_4$-alkoxy;

very preferably halogen.

In a preferred embodiment of the invention, A is a group of the formula —$NR^4R^5$ where the substituents $R^4$ and $R^5$ are each independently hydrogen or $C_1$-$C_6$-alkyl.

In a particularly preferred embodiment of the invention, A is a group of the formula —$NR^4R^5$ where $R^4$ is hydrogen, $C_1$-$C_6$-alkyl, $C_1$-$C_6$-haloalkyl, $C_2$-$C_6$-alkenyl or $C_2$-$C_6$-alkynyl, especially preferably hydrogen or $C_1$-$C_6$-alkyl, very preferably $C_1$-$C_6$-alkyl, more preferably methyl; and $R^5$ is $C_1$-$C_6$-alkyl, $C_1$-$C_4$-haloalkyl, $C_3$-$C_8$-cycloalkyl or phenyl, especially preferably $C_1$-$C_6$-alkyl, very preferably $C_1$-$C_4$-alkyl.

The inventive process steps may be performed either batchwise or continuously in reaction vessels suitable therefor.

In the batchwise procedure, stirred tanks and stirred reactors will typically be used. These are generally equipped with suitable heat exchangers or a cooling jacket to remove the heat of reaction.

The inventive reaction steps are performed continuously likewise in the reactors suitable therefor, for example in stirred tanks, stirred tank batteries and tubular reactors, of which preference is given to reactors having low backmixing.

The amount of solvent or diluent is generally selected such that the reaction mixtures remain free-flowing during the reaction.

The 3-phenyl(thio)uracils and -dithiouracils of the formula I are prepared by reacting a carbamate of the formula II with an enamine of the formula III:

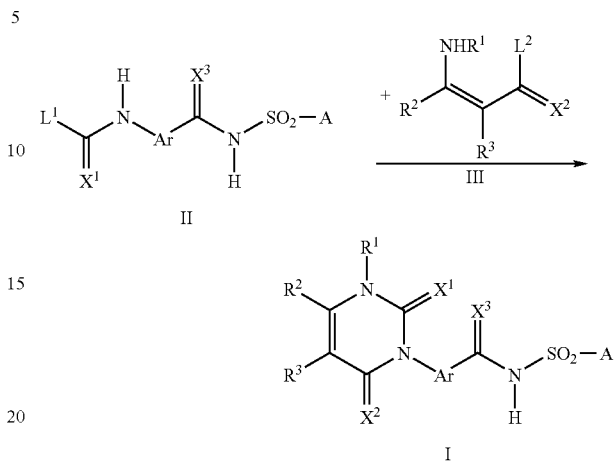

The variables $X^1$, $X^2$, $X^3$, $R^1$, $R^2$, $R^3$ and also Ar and A are each as defined above, and are especially preferably as defined with preference in the description.

$L^1$ is a nucleophilically displaceable leaving group,
preferably $C_1$-$C_6$-alkoxy or $C_1$-$C_6$-alkylthio,
more preferably $C_1$-$C_6$-alkoxy.

$L^2$ is a nucleophilically displaceable leaving group;
preferably $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2$-$C_4$-alkoxy, $C_2$-$C_6$-alkenyloxy, $C_2$-$C_6$-haloalkenyloxy, $C_3$-$C_6$-alkynyloxy, $C_3$-$C_6$-haloalkynyloxy, $C_3$-$C_8$-cycloalkyloxy, $C_1$-$C_6$-cyanoalkoxy or benzyloxy,
which may itself be partly or fully halogenated on the phenyl ring and/or may be substituted by from one to three radicals from the group of cyano, nitro, $C_1$-$C_4$-alkyl, $C_1$-$C_4$-alkoxy and $C_1$-$C_4$-alkylthio;
preferably $C_1$-$C_6$-alkoxy, $C_1$-$C_6$-haloalkoxy, $C_1$-$C_4$-alkoxy-$C_2$-$C_4$-alkoxy, $C_2$-$C_6$-alkenyloxy, $C_2$-$C_6$-haloalkenyloxy, $C_3$-$C_6$-alkynyloxy or $C_3$-$C_6$-haloalkynyloxy; very preferably $C_1$-$C_6$-alkoxy, $C_1$-$C_4$-alkoxy-$C_2$-$C_4$-alkoxy, $C_2$-$C_6$-alkenyloxy or $C_3$-$C_6$-alkynyloxy;
exceptionally preferably $C_1$-$C_6$-alkoxy.

This reaction of the carbamates of the formula II with enamines of the formula III is effected typically at temperatures above room temperature, for example from 25° C. to 200° C., preferably from 90° C. to 190° C., more preferably from 100° C. to 140° C. in an inert organic solvent in the presence of a base (cf., for example, WO 99/31091).

The reaction pressure is of minor importance for the success of the process according to the invention and may, for example, be in the range from 500 mbar to 10 bar. Preference is given to carrying out the reaction in the region of standard pressure, i.e. in the range from 0.9 to 1.2 bar.

The reaction time required for the reaction is generally in the range from 1 h to 24 h, and in particular in the range from 2 h to 8 h.

The reaction may in principle be carried out in substance. However, preference is given to reacting the carbamates of the formula II with the enamines of the formula III in an organic solvent. Suitable in principle are all solvents which are capable of dissolving the carbamates of the formula II and the enamines of the formula III at least partly and preferably fully under reaction conditions. Preferred solvents are polar protic solvents.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, diethylene glycol dimethyl ether, anisole and tetrahydrofuran, nitriles such as acetonitrile and propionitrile, alcohols such as methanol, ethanol, n-propanol, isopropanol, n-butanol and tert-butanol, carboxylic esters such as butyl acetate, and also dimethyl sulfoxide, dimethylformamide, dimethylacetamide and N-methylpyrrolidone; more preferably dimethylformamide, dimethylacetamide and N-methylpyrrolidone.

It is also possible to use mixtures of the solvents mentioned.

Useful bases are generally inorganic compounds such as alkali metal and alkaline earth metal hydroxides such as lithium hydroxide, sodium hydroxide, potassium hydroxide and calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate, sodium carbonate, potassium carbonate, calcium carbonate and cesium carbonate, and also alkali metal hydrogencarbonates such as sodium hydrogencarbonate, organometallic compounds, especially alkali metal alkyls such as methyllithium, butyllithium and phenyllithium, alkali metal and alkaline earth metal alkoxides such as lithium methoxide, sodium methoxide, sodium ethoxide, potassium ethoxide, potassium tert-butoxide, potassium tert-pentoxide and dimethoxymagnesium, and also organic bases, for example tertiary amines such as trimethylamine, triethylamine, diisopropylethylamine and N-methylpiperidine, pyridine, substituted pyridines such as collidine, lutidine and 4-dimethylaminopyridine, and also bicyclic amines. Particular preference is given to alkali metal and alkaline earth metal hydroxides, alkali metal and alkaline earth metal carbonates and also alkali metal and alkaline earth metal alkoxides.

The bases are generally used in excess, more preferably with from 1.1 to 3 equivalents based on the carbamate of the formula II, and they may also be used as the solvent. It may be advantageous to add the base offset over a period of time.

The bases are used preferably at from 1.1 to 2.4 equivalents, very preferably at from 2.2 to 2.4 equivalents, more preferably at 2.3 equivalents, based on the carbamate II.

The reactants are generally reacted with one another in equimolar amounts. It may be advantageous to use one component in an excess based on the other components. Preference is given to using the compounds in a molar II:III ratio in the range from 1.5:1 to 1:1.5, more preferably from 1:1 to 1:1.2, especially preferably from 1:1.

Preference is given to partly removing the compounds $L^1$-H and $L^2$-H formed in the course of the reaction of the carbamates of the formula II with the enamines of the formula III during the reaction, especially when the compounds $L^1$-H and $L^2$-H are a $C_1$-$C_4$-alkanol such as methanol or ethanol. To this end, the reaction will be carried out in a manner known per se at a temperature and a pressure at which the compounds $L^1$-H and $L^2$-H, if appropriate, are distilled out of the reaction mixture as an azeotrope with the solvent. If appropriate, fresh solvent can be introduced into the mixture for compensation or the solvent distilled off with the compounds $L^1$-H and $L^2$-H can be recycled into the reaction after optional distillative depletion of the compounds $L^1$-H and $L^2$-H.

For these reasons, it is advantageous when the solvent used has a boiling point of at least 10° C., in particular at least 30° C., above the boiling point of the compounds $L^1$-H and $L^2$-H formed in the reaction (each at atmospheric pressure).

Appropriately, the reaction of the carbamates of the formula II with the enamines of the formula III is carried out in an apparatus which is equipped with at least one distillation or rectification apparatus, for example a distillation column, which firstly allows the compounds $L^1$-H and $L^2$-H, if appropriate together with the solvent, to be distilled off and simultaneously enables removal and recycling of any solvent distilled off with the compounds $L^1$-H and $L^2$-H.

For the reaction, the compounds II and III may be contacted with one another in any desired manner, i.e. the reactants and the base may be introduced into the reaction vessel separately, simultaneously or successively and reacted. For example, the compounds II and III may be initially charged in a reaction vessel, if appropriate with the desired solvent, and then the desired reaction conditions may be attained. However, it is also possible to introduce the majority or entirety of compounds II and III, if appropriate in a solvent under reaction conditions, into the reaction vessel.

In a preferred embodiment of the invention, the majority, in particular at least 80% and more preferably the entirety or virtually the entirety (>95%) of the carbamates of the formula II are initially charged, and the majority, in particular at least 80% and more preferably the entirety or virtually the entirety (>95%) of the enamine of the formula III is added thereto under reaction conditions in the course of the reaction, for example over a period of from 0.5 to 20 h and in particular from 1 to 10 h. To this end, the enamines of the formula III will preferably be dissolved in a solvent.

In a further preferred embodiment of the invention, the compounds II and III are initially charged and then the majority, in particular at least 80% and more preferably the entirety or virtually the entirety (>95%), of the base is added thereto. The reaction may if appropriate be completed by metering in further base.

The 3-phenyl(thio)uracils and -dithiouracils of the formula I can be isolated from the reaction mixture in a manner known per se.

When the reaction has been carried out in a solvent, the reaction mixture will generally be concentrated and/or cooled and/or a precipitant will be added. Suitable precipitants are solvents in which the 3-phenyl(thio)uracils and -dithiouracils of the formula I dissolve only to a slight extent, if at all, at least at temperatures below 25° C. These include in particular aliphatic and cycloaliphatic hydrocarbons such as pentane, hexane, cyclohexane, heptane, petroleum ether, toluene and the like. The precipitation or crystallization may be followed by further purification measures. When the reaction is carried out as preferred in an alcohol, in particular in methanol or ethanol, or in an alkylbenzene, it is generally unnecessary to add a precipitant.

For the workup, it is also advantageous to adjust the pH of the reaction mixture to pH<7 using acid, preferably using inorganic acids, for example hydrochloric acid or sulfuric acid. In particular, it is advantageous when the pH of the reaction mixture is <2 at the end.

The enamines of the formula III required for the preparation of the 3-phenyl(thio)uracils and -dithiouracils of the formula I are disclosed in the literature (for example A. Lutz, A. and S. Trotto, J. of Heterocyclic Chem. 1972, 9, 3, 513-522) and can be prepared in accordance with the cited literature.

In particular, it is possible by this route to prepare 3-phenyluracils of the formula I.A.1

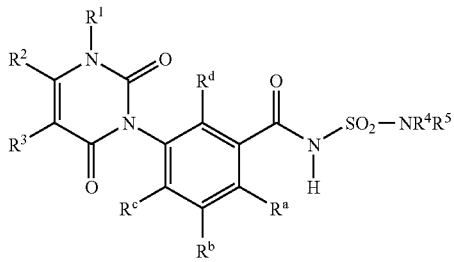

where $R^b$ and $R^d$ are each hydrogen
by reacting corresponding carbamates of the formula II.A.1

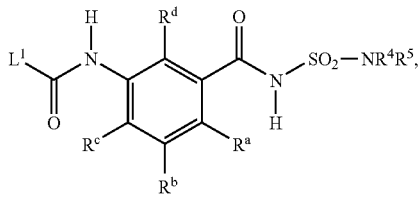

where $R^b$ and $R^d$ are each hydrogen
with enamines of the formula III

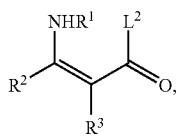

where $X^2$ is oxygen

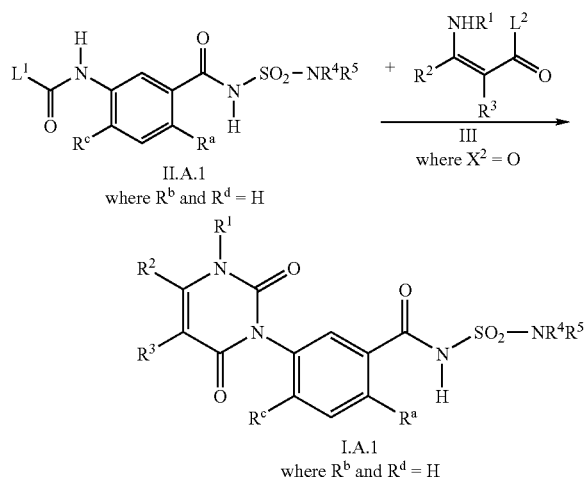

$L^1$ is a nucleophilically displaceable leaving group,
preferably $C_1$-$C_6$-alkoxy or $C_1$-$C_6$-alkylthio,
more preferably $C_1$-$C_6$-alkoxy,
especially preferably $C_1$-$C_4$-alkoxy,
very preferably methoxy or ethoxy;

$L^2$ is a nucleophilically displaceable leaving group;
preferably $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2$-$C_4$-alkoxy, $C_2$-$C_6$-alkenyloxy, $C_2$-$C_6$-haloalkenyloxy, $C_3$-$C_6$-alkynyloxy, $C_3$-$C_6$-haloalkynyloxy, $C_3$-$C_8$-cycloalkyloxy, $C_1$-$C_6$-cyanoalkoxy or benzyloxy,
which may itself be partially or fully halogenated on the phenyl ring and/or be substituted by from one to three radicals from the group of cyano, nitro, $C_1$-$C_4$-alkyl, $C_1$-$C_4$-alkoxy and $C_1$-$C_4$-alkylthio;
preferably $C_1$-$C_6$-alkoxy, $C_1$-$C_6$-haloalkoxy, $C_1$-$C_4$-alkoxy-$C_2$-$C_4$-alkoxy, $C_2$-$C_6$-alkenyloxy, $C_2$-$C_6$-haloalkenyloxy, $C_3$-$C_6$-alkynyloxy or $C_3$-$C_6$-haloalkynyloxy;
very preferably $C_1$-$C_6$-alkoxy, $C_1$-$C_4$-alkoxy-$C_2$-$C_4$-alkoxy, $C_2$-$C_6$-alkenyloxy or $C_3$-$C_6$-alkynyloxy;
exceptionally preferably $C_1$-$C_6$-alkoxy.

Preference is given to the preparation especially of those 3-phenyluracils of the formula I.A.1 where $R^b$ and $R^d$=hydrogen, in which the variables $R^1$, $R^2$, $R^3$, $R^a$, $R^c$, and also $R^4$ and $R^5$, each alone or in combination with one another, are defined as follows:

$R^1$ is hydrogen, $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl;
very preferably hydrogen or $C_1$-$C_4$-alkyl,
more preferably hydrogen, methyl or ethyl,
especially preferably methyl;
likewise preferably hydrogen, amino or $C_1$-$C_4$-alkyl,
more preferably hydrogen, amino, methyl or ethyl,
especially preferably amino or methyl;
likewise preferably hydrogen, amino or $C_1$-$C_4$-alkyl,
more preferably hydrogen or amino,
especially preferably hydrogen;

$R^2$ is hydrogen, $C_1$-$C_4$-alkyl or $C_1$-$C_4$-haloalkyl,
more preferably hydrogen, methyl, difluoromethyl or trifluoromethyl,
especially preferably trifluoromethyl;

$R^3$ is hydrogen or $C_1$-$C_4$-alkyl,
more preferably hydrogen.

$R^a$ is hydrogen, halogen or cyano,
especially preferably hydrogen, fluorine, chlorine or cyano,
very preferably hydrogen, chlorine or cyano,
exceptionally preferably hydrogen or chlorine,
very exceptionally preferably hydrogen;

$R^c$ is hydrogen or halogen,
especially preferably hydrogen, fluorine or chlorine,
very preferably hydrogen or fluorine,
exceptionally preferably fluorine;

$R^4$ and $R^5$ are each independently
hydrogen or $C_1$-$C_6$-alkyl which may itself be substituted by a substituent selected from the group of halogen, cyano and $C_1$-$C_4$-alkoxy, preferably halogen;
especially preferably
$R^4$ is hydrogen, $C_1$-$C_6$-alkyl, $C_2$-$C_6$-alkenyl or $C_2$-$C_6$-alkynyl,
very preferably hydrogen or $C_1$-$C_6$-alkyl,
more preferably $C_1$-$C_4$-alkyl,
exceptionally preferably methyl; and
$R^5$ is $C_1$-$C_6$-alkyl, $C_3$-$C_8$-cycloalkyl or phenyl,
very preferably $C_1$-$C_6$-alkyl,
more preferably $C_1$-$C_4$-alkyl.

In particular, 3-phenyl(thio)uracils and -dithiouracils of the formula I where
R$^1$ is C$_1$-C$_6$-alkyl, C$_1$-C$_4$-cyanoalkyl, C$_1$-C$_6$-haloalkyl, C$_3$-C$_8$-cycloalkyl, C$_2$-C$_6$-alkenyl, C$_2$-C$_6$-haloalkenyl, C$_3$-C$_6$-alkynyl, C$_3$-C$_6$-haloalkynyl, phenyl-C$_1$-C$_4$-alkyl or amino;
can be prepared by reacting carbamates of the formula II

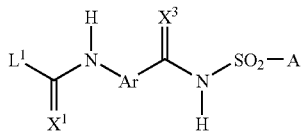

where the variables X$^1$, X$^3$, Ar and A are each as defined above and L$^1$ is a nucleophilically displaceable leaving group with enamines of the formula III

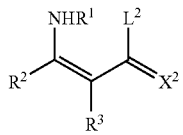

where R$^1$ is hydrogen, the variables X$^2$, R$^2$ and R$^3$ are each as defined above and L$^2$ is a nucleophilically displaceable leaving group; and
then reacting the resulting 3-phenyl(thio)uracil and -dithiouracil of the formula I where R$^1$ is hydrogen
with an alkylating agent of the formula VI

 R$^1$-L$^4$    VI where R$^1$ is C$_1$-C$_6$-alkyl, C$_1$-C$_4$-cyanoalkyl, C$_1$-C$_6$-haloalkyl, C$_3$-C$_8$-cycloalkyl, C$_2$-C$_6$-alkenyl, C$_2$-C$_6$-haloalkenyl, C$_3$-C$_6$-alkynyl, C$_3$-C$_6$-haloalkynyl or phenyl-C$_1$-C$_4$-alkyl; and
L$^4$ is a nucleophilically displaceable leaving group;
to give 3-phenyl(thio)uracils and -dithiouracils of the formula I where R$^1$ is C$_1$-C$_6$-alkyl, C$_1$-C$_4$-cyanoalkyl, C$_1$-C$_6$-haloalkyl, C$_3$-C$_8$-cycloalkyl, C$_2$-C$_6$-alkenyl, C$_2$-C$_6$-haloalkenyl, C$_3$-C$_6$-alkynyl, C$_3$-C$_6$-haloalkynyl or phenyl-C$_1$-C$_4$-alkyl;
or
with an aminating agent of the formula VII

 H$_2$N-L$^5$    VII where L$^5$ is a nucleophilically displaceable leaving group to give 3-phenyl(thio)uracils and -dithiouracils of the formula I where R$^1$ is NH$_2$.

For the preparation of the 3-phenyl(thio)uracils and -dithiouracils of the formula I where R$^1$ is hydrogen, the aforementioned reaction conditions, especially the reaction conditions mentioned above as preferred, apply.

L$^4$ in the alkylating agent of the formula VI is a nucleophilically displaceable leaving group,
preferably halogen, hydrogensulfate, C$_1$-C$_6$-alkylsulfate, sulfate, C$_1$-C$_6$-alkyl-sulfonyloxy, C$_1$-C$_6$-haloalkylsulfonyloxy or phenylsulfonyloxy,
where the phenyl ring is optionally mono- or polysubstituted by halogen, nitro, C$_1$-C$_6$-alkyl or C$_1$-C$_6$-haloalkyl,
more preferably halogen, hydrogensulfate, C$_1$-C$_6$-alkylsulfonyloxy, C$_1$-C$_6$-haloalkylsulfonyloxy, phenylsulfonyloxy, p-toluenesulfonyloxy, p-chlorophenylsulfonyloxy, p-bromophenylsulfonyloxy or p-nitrophenylsulfonyloxy, especially preferably chlorine, methylsulfonyloxy, trifluoromethylsulfonyloxy or phenylsulfonyloxy.

L$^5$ in the aminating agent of the formula VII is a nucleophilically displaceable leaving group,
preferably halogen, hydrogensulfate, C$_1$-C$_6$-alkylsulfonyloxy, C$_1$-C$_6$-haloalkylsulfonyloxy, phenylsulfonyloxy or phenyloxy,
where the phenyl ring is optionally mono- or polysubstituted by halogen, nitro, C$_1$-C$_6$-alkyl or C$_1$-C$_6$-haloalkyl,
more preferably halogen, hydrogensulfate, C$_1$-C$_6$-alkylsulfonyloxy, C$_1$-C$_6$-halo-alkylsulfonyloxy, phenylsulfonyloxy, p-toluenesulfonyloxy, p-chlorophenyl-sulfonyloxy, p-bromophenylsulfonyloxy or p-nitrophenylsulfonyloxy, especially preferably chlorine, methylsulfonyloxy, trifluoromethylsulfonyloxy or phenylsulfonyloxy.

The process for alkylating or aminating the compound I where R$^1$=hydrogen is surprising in that the formation of corresponding N-alkylsulfonamides or mixtures of N-alkylsulfonamides or N-alkyl-substituted (thio)uracils or dithiouracils would have been expected. It is known that sulfuric diamides are alkylated in a simple manner with sulfuric diesters or arenesulfonic esters in the presence of a base; see, for example, R. Sowada, J. Prakt. Chem. 25, 88 (1964). In the case of trisubstituted sulfuric diamides, the formation of tetrasubstituted sulfuric diamides is known; see B. Unterhalt, E. Seebach, Arch. Pharm. 314, 51 (1981). It is likewise possible to alkylate sulfuric diamides in which the amide function already carries an acyl radical; see K. C. C. Bancroft et al., J. Heterocycl. Chem. 15, 1521 (1978); A. Martinex et al., Bioorg. Med. Chem. Lett. 9 (21), 3133 (1999). The person skilled in the art would therefore have expected, owing to the easy alkylatability of the sulfamide side chain, the preferred alkylation on the sulfonamide nitrogen atom or at least the formation of dialkylated products.

The N-alkylation of the compound I on the free (thio)uracil nitrogen atom succeeds in a manner known per se for uracils by reacting the compound I where R$^1$=hydrogen with an alkylating agent R$^1$-L$^4$ (VI), as described, for example, in U.S. Pat. No. 4,943,309, whose disclosure on alkylation is hereby incorporated fully by reference.

Preferred alkylating agents are C$_1$-C$_4$-alkyl halides, di-C$_1$-C$_4$-alkyl sulfates, C$_1$-C$_4$-alkyl phenylsulfonates where the phenyl radical is optionally mono- or disubstituted by halogen, nitro or C$_1$-C$_6$-alkyl. Particularly preferred alkylating agents are methylating agents or ethylating agents such as dimethyl sulfate, diethyl sulfate, methyl iodide, ethyl iodide, methyl bromide, methyl chloride, ethyl bromide, ethyl chloride, methyl or ethyl C$_1$-C$_6$-alkylsulfonate, or the methyl or ethyl esters of the aforementioned phenylsulfonic acids. A very particularly preferred methylating agent is dimethyl sulfate.

In the process according to the invention, the alkylating agent can be used either in an equimolar amount based on the compound I, or in a substoichiometric amount or superstoichiometric amount. Typically, at least an equimolar amount of alkylating agent VI based on the compound I is used. The molar ratios in which the compound I where R$^1$=hydrogen is used relative to alkylating agent VI are in the range from 1:1 to 1:3, preferably from 1:1 to 1:1.3, for the ratio of compound I to alkylating agent VI.

Typically, the alkylation is performed in the presence of a base. Useful bases are in principle all compounds which are capable of deprotonating the lactam nitrogen atom. Suitable bases are, for example, the bases mentioned in connection with the preparation of the compound I by reacting II with III. The base is preferably selected from alkali metal and alkaline earth metal hydroxides such as sodium hydroxide, potassium hydroxide and lithium hydroxide, alkali metal and alkaline earth metal oxides such as calcium oxide, alkali metal and alkaline earth metal carbonates such as lithium carbonate, sodium carbonate, potassium carbonate, cesium carbonate, magnesium carbonate, calcium carbonate, zinc carbonate or barium carbonate. In a particularly preferred embodiment of the process according to the invention, the base used is sodium hydroxide or potassium carbonate.

The base can be used in a substoichiometric, superstoichiometric or equimolar amount based on the compound I. Preference is given to using at least an equimolar amount of base based on the compound I. The amount of base will generally not be more than 1.3 mol based on 1 mol of the compound I.

The reaction of the compounds I where $R^1$=hydrogen with the alkylating agent of the formula VI is advantageously performed in the presence of a solvent. Depending on the temperature range, the solvents used for these reactions are aliphatic, cycloaliphatic or aromatic hydrocarbons such as pentane, hexane, cyclopentane, cyclohexane, toluene, xylene, chlorinated aliphatic and aromatic hydrocarbons such as dichloromethane, trichloromethane, 1,2-dichloroethane, 1,1,2,2-tetrachloroethane, chlorobenzene, 1,2-, 1,3- or 1,4-dichlorobenzene, chlorotoluenes, dichlorotoluenes, open-chain dialkyl ethers such as diethyl ether, di-n-propyl ether, di-n-isopropyl ether, methyl tert-butyl ether, cyclic ethers such as tetrahydrofuran, 1,4-dioxane, anisole, glycol ethers such as dimethyl glycol ether, diethylene glycol ether, diethylene glycol dimethyl ether, diethylene glycol diethyl ether, $C_1$-$C_4$-alcohols such as methanol, ethanol, n-propanol, isopropanol, n-butanol, ketones such as acetone, methyl ethyl ketone, methyl isopropyl ketone, methyl isobutyl ketone, butanone, carbonates such as diethyl carbonate and ethylene carbonate, N,N-dialkylamides such as N,N-dimethylformamide or N,N-dimethylacetamide, N-alkyllactams such as N-methylpyrrolidone, sulfoxides such as dimethyl sulfoxide, tetralkylureas such as tetramethylurea, tetraethylurea, tetrabutylureas, dimethylethyleneurea, dimethylpropyleneurea, or mixtures of these solvents. Preferred solvents are N,N-dimethylformamide, N-methylpyrrolidone, acetone, dichloromethane, tetrahydrofuran, toluene or mixtures of these solvents.

The alkylation of the compound I is preferably performed at temperatures between −5° C. and 100° C., preferably at temperatures between 0° C. and 80° C. and especially at temperatures between 20° C. and 50° C. The reaction time can be determined by the person skilled in the art in a manner familiar per se by routine methods such as thin-layer chromatography or HPLC.

The compound I, alkylating agent VI and base can be added separately, simultaneously or successively.

Advantageously, the multistage process for preparing the compound I where $R^1$≠hydrogen can also be performed as a one-pot reaction. In the reaction of the carbamates of the formula II with the enamine of the formula III where $R^1$=hydrogen in the presence of an excess of base, the uracil salt is formed initially and is then, without isolation or purification, reacted with the alkylating agent of the formula VI. Thereafter, the reaction is conducted to completion within the specified temperature range.

In another variant of the process according to the invention, the reaction can also be performed in an aqueous multiphasic system, preferably in the presence of phase transfer catalysts such as quaternary ammonium salts or phosphonium salts. Suitable quaternary ammonium salts comprise tetraalkyl($C_1$-$C_{18}$)ammonium chlorides, bromides, fluorides or tetrafluoroborates, such as tetraethylammonium chloride, tetrabutylammonium bromide, tetrabutylammonium iodide, tetrabutylammonium tetrafluoroborate, N-benzyltrialkyl($C_1$-$C_{18}$)ammonium chlorides, bromides or fluorides such as benzyltriethylammonium chloride, preferably tetrabutylammonium bromide or tetrabutylammonium iodide. Suitable phosphonium salts are, for example, tetraphenylphosphonium chloride or bromide, tetraalkyl($C_1$-$C_{18}$)phosphonium chloride or bromide such as tetrabutylphosphonium bromide. In general, the phase transfer catalyst is used in an amount of up to 20 mol %, preferably between 1 and 15 mol % and in particular between 2 and 12 mol %, based on the compound I where $R^1$=hydrogen.

The multiphasic system comprises an aqueous phase and at least one organic liquid phase. In addition, solid phases may also occur in the course of the reaction. The aqueous phase is preferably a solution of alkali metal or alkaline earth metal hydroxides or carbonates in water. With regard to suitable alkali metal or alkaline earth metal hydroxides or carbonates, reference is made to the statements above. Particular preference is given to using alkali metal or alkaline earth metal hydroxides, especially sodium hydroxide. Useful solvents for the organic phase are preferably aliphatic, cycloaliphatic or aromatic, optionally halogenated hydrocarbons, cyclic or open-chain ethers or mixtures thereof, reference being made to the statements above with regard to the aliphatic, cycloaliphatic or aromatic, optionally halogenated hydrocarbons, cyclic or open-chain ethers. In a preferred embodiment of the process according to the invention, the multiphasic system consists of aqueous sodium hydroxide solution as the aqueous phase and of toluene and tetrahydrofuran or dichloromethane and tetrahydrofuran as the organic phase.

When a multiphasic system is used, it is possible, for example, to initially charge the compound I in one of the aforementioned organic solvents or solvent mixtures. Thereafter, the aqueous solution of the base, the alkylating agent VI and the phase transfer catalyst is added with mixing and then the reaction is brought to completion within the temperature range specified.

The reaction can be performed at standard pressure, reduced pressure or under elevated pressure, if appropriate under inert gas, continuously or batchwise.

In particular, it is possible by this route to prepare 3-phenyluracils of the formula I.A.1

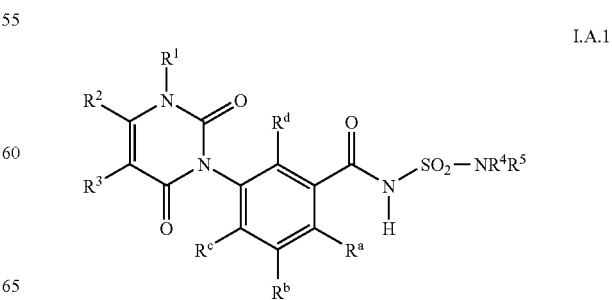

I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen by reacting corresponding carbamates of the formula II.A.1

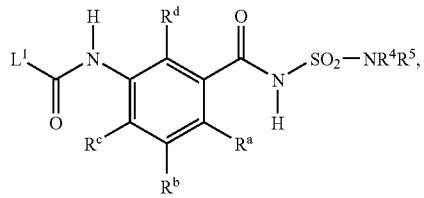

where $R^b$ and $R^d$ are each hydrogen with enamines of the formula III

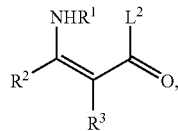

where $R^1$ is hydrogen; and
$X^2$ is oxygen, and then alkylating the 3-phenyluracil of the formula I.A.1 thus formed, where $R^1$, $R^b$ and $R^d$ are each hydrogen, with an alkylating agent of the formula VI $$R^1\text{-}L^4 \quad \text{VI}$$

where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $L^4$ is a nucleophilically displaceable leaving group, preferably the definitions specified above as preferred;

to give 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen:

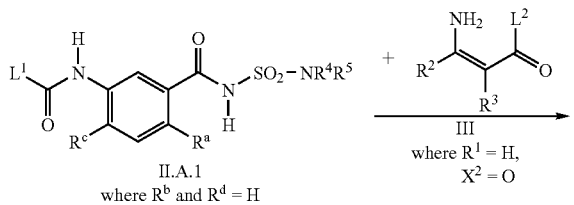

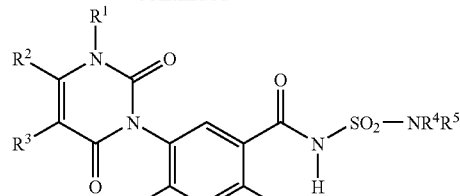

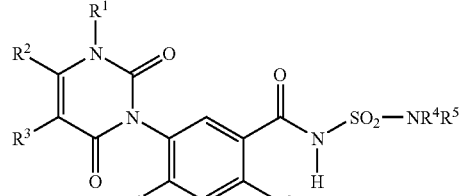

$L^1$ is a nucleophilically displaceable leaving group,
preferably $C_1$-$C_6$-alkoxy or $C_1$-$C_6$-alkylthio,
more preferably $C_1$-$C_6$-alkoxy,
especially preferably $C_1$-$C_4$-alkoxy,
very preferably methoxy or ethoxy;

$L^2$ is a nucleophilically displaceable leaving group;
preferably $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2$-$C_4$-alkoxy, $C_2$-$C_6$-alkenyloxy, $C_2$-$C_6$-haloalkenyloxy, $C_3$-$C_6$-alkynyloxy, $C_3$-$C_6$-haloalkynyloxy, $C_3$-$C_8$-cycloalkyloxy, $C_1$-$C_6$-cyanoalkoxy or benzyloxy,
which may itself be partially or fully halogenated on the phenyl ring and/or be substituted by from one to three radicals from the group of cyano, nitro, $C_1$-$C_4$-alkyl, $C_1$-$C_4$-alkoxy and $C_1$-$C_4$-alkylthio;
preferably $C_1$-$C_6$-alkoxy, $C_1$-$C_6$-haloalkoxy, $C_1$-$C_4$-alkoxy-$C_2$-$C_4$-alkoxy, $C_2$-$C_6$-alkenyloxy, $C_2$-$C_6$-haloalkenyloxy, $C_3$-$C_6$-alkynyloxy or $C_3$-$C_6$-haloalkynyloxy;
very preferably $C_1$-$C_6$-alkoxy, $C_1$-$C_4$-alkoxy-$C_2$-$C_4$-alkoxy, $C_2$-$C_6$-alkenyloxy or $C_3$-$C_6$-alkynyloxy;
exceptionally preferably $C_1$-$C_6$-alkoxy.

Preference is given to the preparation especially of those 3-phenyluracils of the formula I.A.1 where $R^b$ and $R^d$=hydrogen, in which the variables $R^1$, $R^2$, $R^3$, $R^a$, $R^c$, and also $R^4$ and $R^5$, each alone or in combination with one another, are defined as follows:

$R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl;
very preferably $C_1$-$C_4$-alkyl,
more preferably methyl or ethyl,
especially preferably methyl;

$R^2$ is hydrogen, $C_1$-$C_4$-alkyl or $C_1$-$C_4$-haloalkyl,
more preferably hydrogen, methyl, difluoromethyl or trifluoromethyl, especially preferably trifluoromethyl;

$R^3$ is hydrogen or $C_1$-$C_4$-alkyl,
more preferably hydrogen.

$R^a$ is hydrogen, halogen or cyano,
especially preferably hydrogen, fluorine, chlorine or cyano, very preferably hydrogen, chlorine or cyano,
exceptionally preferably hydrogen or chlorine,
very exceptionally preferably hydrogen;
$R^c$ is hydrogen or halogen,
especially preferably hydrogen, fluorine or chlorine,
very preferably hydrogen or fluorine,
exceptionally preferably fluorine;
$R^4$ and $R^5$ are each independently
hydrogen or $C_1$-$C_6$-alkyl which may itself be substituted by a substituent selected from the group of halogen, cyano and $C_1$-$C_4$-alkoxy, preferably halogen;
especially preferably
$R^4$ is hydrogen, $C_1$-$C_6$-alkyl, $C_2$-$C_6$-alkenyl or $C_2$-$C_6$-alkynyl,
very preferably hydrogen or $C_1$-$C_6$-alkyl,
more preferably $C_1$-$C_4$-alkyl,
exceptionally preferably methyl; and
$R^5$ is $C_1$-$C_6$-alkyl, $C_3$-$C_8$-cycloalkyl or phenyl,
very preferably $C_1$-$C_6$-alkyl,
more preferably $C_1$-$C_4$-alkyl.

The introduction of the amino group on the (thio)uracil ring or dithiouracil ring succeeds surprisingly on the basis of known processes for introducing the amino group on the uracil nitrogen. Such processes are described, for example, in DE 196 52431, whose disclosure on electrophilic amination is hereby incorporated fully by reference. Suitable aminating agents of the formula VII include, for example, 1-aminooxy-2,4-dinitro-benzene or O-mesitylenesulfonylhydroxylamine.

If appropriate, the reaction is effected in the presence of a base. Useful bases include all customary inorganic or organic bases. Suitable bases are, for example, the bases mentioned in connection with the preparation of the compound I by reacting II with III. Preferred bases are alkali metal alkoxides, especially lithium, sodium or potassium alkoxides such as sodium methoxide, sodium ethoxide, lithium ethoxide, potassium methoxide, potassium ethoxide, potassium tert-butoxide, sodium tert-butoxide, sodium isopropoxide, potassium tert-pentoxide, alkali metal hydrides such as sodium hydride, potassium hydride, alkali metal carbonates such as lithium carbonate, sodium carbonate, potassium carbonate, cesium carbonate or tertiary amines, especially amidine bases such as 1,8-diazabicyclo[5.4.0]undec-7-ene. In general, the compound I where $R^1$=hydrogen and the base are used in approximately equimolar amounts.

The reaction of the compound I where $R^1$=hydrogen with an aminating reagent of the formula VII is effected generally in an inert organic solvent or solvent mixture. Solvents preferred for this purpose are nitriles such as acetonitrile, propionitrile or butyronitrile, ketones such as acetone and methyl ethyl ketone, carbonates such as dimethyl carbonate, diethyl carbonate and ethylene carbonate, and also amides such as N,N-dimethylformamide, N,N-dimethylacetamide and N-methylpyrrolidone. Also suitable are organic solvents having basic character, for example the aforementioned tertiary amines such as trialkylamines and pyridine compounds.

In general, the reaction will be performed at temperatures of from 0 to 80° C., preferably between 10 and 60° C. For this purpose, the compound I where $R^1$=hydrogen and the aminating reagent of the formula VII are generally reacted in approximately equimolar amounts. However, it is also possible to use one of the components in a relatively large excess, in which case the excess will preferably not be more than 50 mol % based on the component present in deficiency.

The workup of the reaction mixture to obtain the target product I can be effected by the methods customary for this purpose. Generally, the solvent used will be removed by customary processes, for example by distillation. The target compound I can then be taken up in a water-immiscible organic solvent, any impurities can be extracted with optionally acidified water, the mixture can be dried and the solvent can be removed under reduced pressure. For further purification, the customary processes such as crystallization, precipitation or chromatography can be employed. When a biphasic system is used, workup will generally be effected by extraction.

Compounds of the formula I where one of the $X^1$, $X^2$ or $X^3$ radicals, or the $X^1$, $X^2$ and $X^3$ radicals, are each oxygen can be converted to compounds of the general formula I where one of the $X^1$, $X^2$ or $X^3$ radicals, or the $X^1$, $X^2$ and $X^3$ radicals, are each sulfur by known methods by treating with sulfurizing agents. Examples of suitable sulfurizing agents are organophosphorus sulfides such as the Lawesson reagent, organotin sulfides or phosphorus(V) sulfides (see also J. March, Advanced Organic Synthesis, 2nd edition, Wiley Interscience 1985, p. 794 and literature cited there). The reaction can be performed in a solvent or in bulk. Suitable solvents are the above-mentioned inert solvents, and also basic solvents such as pyridine and comparable solvents. The temperature required for the reaction is generally above room temperature and is in particular in the range from 50 to 200° C. When the reaction of the enamine III with an isothiocyanate II in which the $X^1$ radical is sulfur is performed, the corresponding 2-thioxouracils where $X^1$=sulfur are obtained directly.

The carbamates of the formula II required for the preparation of the 3-phenyl(thio)uracils and -dithiouracils of the formula I are obtainable by reacting an amine of the formula IV with a compound of the formula V:

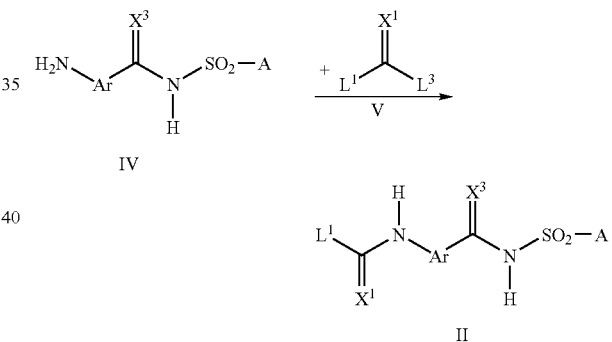

The variables $X^1$, $X^3$, Ar, A and $L^1$ are each as defined above, and especially preferably as defined with preference in the description.

$L^3$ is a nucleophilically displaceable leaving group,
preferably chlorine or $C_1$-$C_6$-alkoxy;
more preferably chlorine.

The amines of the formula IV are reacted with compounds of the formula V typically at temperatures of from −10° C. to 160° C., preferably from 0° C. to 130° C., very preferably from 25° C. to 130° C., in an inert organic solvent, if appropriate in the presence of a base (for example Houben-Weyl, Methoden der organischen Chemie, E5, 1985, p. 972-980, and also VIII, p. 655 and XI Part 2, p. 10).

The reaction pressure is of minor importance for the success of the process according to the invention and may, for example, be in the range from 500 mbar to 10 bar. Preference is given to carrying out the reaction in the region of standard pressure, i.e. in the range from 0.9 to 1.2 bar.

The reaction time required for the reaction is generally in the range from 1 h to 24 h, and in particular in the range from 2 h to 8 h.

The reaction may in principle be carried out in substance. However, preference is given to reacting the amines of the formula IV with the compounds of the formula V in an organic solvent. Suitable in principle are all solvents which are capable of dissolving the compounds IV and V at least partly and preferably fully under reaction conditions.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as methylene-chloride, chloroform and chlorobenzene, ethers such as diethyl ether, diisopropyl ether, tert-butyl methyl ether, dioxane, anisole and tetrahydrofuran, carboxylic esters such as butyl acetate, more preferably halogenated hydrocarbons and ethers.

It is also possible to use mixtures of the solvents mentioned.

The reaction of the amines of the formula IV with compounds of the formula V may be carried out in the presence of a base, but it is not necessary to use a base.

Useful bases are generally inorganic compounds such as alkali metal and alkaline earth metal hydroxides such as lithium hydroxide, sodium hydroxide, potassium hydroxide and calcium hydroxide, alkali metal amides such as lithium amide, sodium amide and potassium amide, alkali metal and alkaline earth metal carbonates such as lithium carbonate, potassium carbonate and calcium carbonate, and also alkali metal hydrogencarbonates such as sodium hydrogencarbonate, and also alkali metal and alkaline earth metal alkoxides such as sodium methoxide, sodium ethoxide, potassium ethoxide, potassium tert-butoxide, potassium tert-pentoxide and dimethoxymagnesium, and also organic bases, for example tertiary amines such as trimethylamine, triethylamine, diisopropylethylamine, N-methylpiperidine and N-methylmorpholine, pyridine, substituted pyridines such as picoline, collidine, lutidine and 4-dimethylaminopyridine, and also bicyclic amines. Particular preference is given to organic bases such as triethylamine, pyridine and picoline.

The bases are generally used in equimolar amounts, but they may also be used catalytically, in excess or, if appropriate, as the solvent.

In a preferred variant of the process according to the invention, the amines of the formula IV are reacted with compounds of formula V in the absence of a base.

Some of the advantages of this preferred variant of the reaction are that a complicated workup after the end of the reaction is dispensed with and the further reaction of the carbamates II thus prepared to give 3-phenyl(thio)uracils and -dithiouracils 1, preferably 3-phenyluracils I.A.1, in which case the aforementioned chlorination of the carbamate II can also be performed if appropriate, can be effected as a one-pot reaction or entails only one solvent exchange.

The reactants are generally reacted with one another in equimolar amounts. It may be advantageous to use V in an excess based on IV. Preference is given to using the compounds in a molar IV:V ratio in the range from 1.6:1 to 1:1.6, in particular from 1:1.4 to 1:1.

Preference is given to removing the compound $L^3$-H formed in the reaction of the amines of the formula IV with the compounds of the formula V from the reaction mixture during the reaction to an extent of at least 80%, especially when the compound $L^3$-H is a $C_1$-$C_4$-alkanol such as methanol or ethanol.

To this end, the reaction will be carried out in a manner known per se at a temperature and a pressure at which the compound $L^3$-H, if appropriate, is distilled out of the reaction mixture as an azeotrope with the solvent. If appropriate, fresh solvent will be introduced into the reaction for compensation or the solvent distilled off with the compound $L^3$-H, if appropriate after distillative depletion of the compound $L^3$-H, will be recycled into the reaction.

For these reasons, it is advantageous when the solvent used has a boiling point of at least 10° C. and in particular at least 30° C. above the boiling point of the compound $L^3$-H formed in the reaction (each at standard pressure).

Appropriately, the reaction of the amines of the formula IV with the compounds of the formula V is carried out in an apparatus which is equipped with at least one distillation and rectification apparatus, for example a distillation column, which firstly allows the compound $L^3$-H, if appropriate together with the solvent, to be distilled off and simultaneously enables removal and recycling of any solvent distilled off with the compound $L^3$-H.

For the reaction, the amines of the formula IV may be contacted with the compounds of the formula V and, if appropriate, the base in any desired manner, i.e. the reactants and, if appropriate, the base may be introduced into the reaction vessel separately, simultaneously or successively and reacted. For example, the amines IV and the compounds V may be initially charged in a reaction vessel, if appropriate with the desired solvent, and then the desired reaction conditions can be attained.

However, it is also possible to introduce the majority or entirety of amine IV and compound V, if appropriate in a solvent, under reaction conditions into the reaction vessel.

In a particularly preferred embodiment, the amine IV is initially charged and then, if appropriate, the base and thereafter the compound V are added.

In a particularly preferred embodiment of the invention, the majority, in particular at least 80% and more preferably the entirety or virtually the entirety (>95%) of the amines of the formula IV are initially charged and the majority, in particular at least 80% and more preferably the entirety or virtually the entirety (>95%) of the compounds of the formula V are added thereto under reaction conditions in the course of the reaction, for example over a period of from 0.5 to 20 h and in particular from 1 to 10 h. To this end, the compounds of the formula V will preferably be dissolved in a solvent. If appropriate, a certain continued reaction time, for example from 1 h to 10 h, in particular from 2 h to 5 h, will be allowed after the addition of the compounds of the formula V.

The carbamates of the formula II can be worked up and isolated in a manner known per se.

In particular, it is possible by this route to prepare carbamates of the formula II.A.1

II.A.1

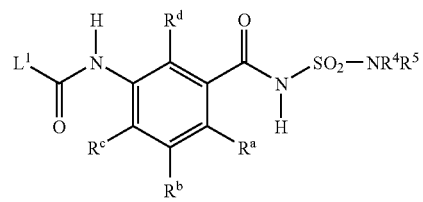

where $R^b$ and $R^d$ are each hydrogen by reacting corresponding amines of the formula IV.A.1

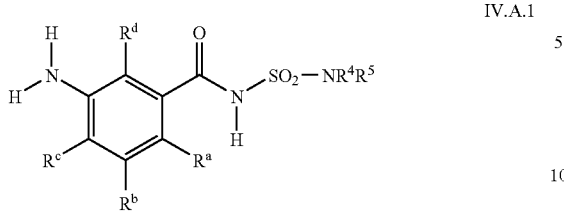

where $R^b$ and $R^d$ are each hydrogen
with compounds V

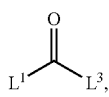

where $X^1$ is oxygen:

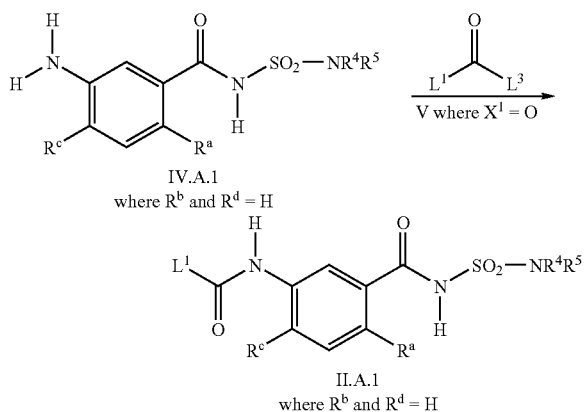

$L^3$ is a nucleophilically displaceable leaving group,
preferably chlorine or $C_1$-$C_6$-alkoxy;
more preferably chlorine.

Preference is given to the preparation especially of those carbamates of the formula II.A.1 where $R^b$ and $R^d$=hydrogen in which the variables $L^1$, $R^a$, $R^c$ and also $R^4$ and $R^5$, each alone and also in combination with one another, are defined as follows:

$L^1$ is a nucleophilically displaceable leaving group,
preferably $C_1$-$C_6$-alkoxy or $C_1$-$C_6$-alkylthio,
more preferably $C_1$-$C_6$-alkoxy,
especially preferably $C_1$-$C_4$-alkoxy,
very preferably methoxy or ethoxy;

$R^a$ is hydrogen, halogen or cyano,
especially preferably hydrogen, fluorine, chlorine or cyano,
very preferably hydrogen, chlorine or cyano,
exceptionally preferably hydrogen or chlorine,
very exceptionally preferably hydrogen;

$R^c$ is hydrogen or halogen,
especially preferably hydrogen, fluorine or chlorine,
very preferably hydrogen or fluorine,
exceptionally preferably fluorine;

$R^4$ and $R^5$ are each independently
hydrogen or $C_1$-$C_6$-alkyl which may in turn be substituted by a substituent selected from the group of
halogen, cyano and $C_1$-$C_4$-alkoxy, preferably halogen;
especially preferably
$R^4$ is hydrogen, $C_1$-$C_6$-alkyl, $C_2$-$C_6$-alkenyl or $C_2$-$C_6$-alkynyl,
very preferably hydrogen or $C_1$-$C_6$-alkyl,
more preferably $C_1$-$C_4$-alkyl,
exceptionally preferably methyl; and
$R^5$ is $C_1$-$C_6$-alkyl, $C_3$-$C_8$-cycloalkyl or phenyl,
very preferably $C_1$-$C_6$-alkyl,
more preferably $C_1$-$C_4$-alkyl.

The amines of the formula IV required for the preparation of the carbamates of the formula II are disclosed in the literature (for example WO 04/039768) or can be prepared in accordance with the cited literature.

The compounds of the formula V required for the preparation of the carbamates of the formula II are disclosed in the literature (for example Houben-Weyl, Methoden der organischen Chemie, E4, 1983, p. 6-17) and can be purchased commercially or prepared in accordance with the cited literature.

The carbamates of the formula II prepared by this route may subsequently, if desired, be halogenated on the Ar radical in an intermediate step before the reaction with the enamines of the formula III.

The carbamates of the formula II prepared by this route may preferably be chlorinated or brominated, very preferably chlorinated, on the Ar radical in a further step.

The halogenation is effected typically at temperatures of from 0° C. to 100° C., preferably from 20° C. to 0.70° C., in an inert organic solvent, if appropriate in the presence of a catalyst (for example Buehler, Peason, Survey of Organic Synthesis, Interscience Publishers 1970, p. 392-404).

The reaction pressure is of minor importance for the success of the process according to the invention and may, for example, be in the range from 500 mbar to 10 bar. Preference is given to carrying out the reaction in the region of standard pressure, i.e. in the range from 0.9 to 1.2 bar.

The reaction time required for the reaction is generally in the range from 1 h to 24 h, and in particular in the range from 3 h to 12 h.

The reaction may in principle be carried out in substance. However, preference is given to reacting the carbamates of the formula V with the halogenating agent in an organic solvent. Suitable in principle are all solvents which are capable of dissolving the compound V at least partly and preferably fully under reaction conditions.

Suitable solvents are aliphatic hydrocarbons such as pentane, hexane, cyclohexane and mixtures of $C_5$-$C_8$-alkanes, halogenated hydrocarbons such as methylene chloride, chloroform, butyl chloride and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, carboxylic acids such as formic acid or acetic acid, esters such as butyl acetate or dimethyl carbonate, and also sulfuryl chloride, more preferably halogenated hydrocarbons and sulfuryl chloride.

It is also possible to use mixtures of the solvents mentioned.

The halogenating agents required for the halogenation are disclosed in the literature (for example Buehler, Peason, Survey of Organic Synthesis, Interscience Publishers 1970, p. 392-404) or can be prepared in accordance with the cited literature.

Examples of halogenating agents which find use are chlorine, N-chlorosuccinimide, $SO_2Cl_2$, $HCl/H_2O_2$, 1,3-dichloro-5,5-dimethylhydantoin, bromine, N-bromosuccinimide, $HBr/H_2O_2$ or 1,3-dibromo-5,5-dimethylhydantoin.

The halogenation of the carbamates of the formula II may, depending upon the halogenating agent selected, be carried out in the presence of a catalyst. Examples of catalysts which find use are Lewis acids such as boron trifluoride, aluminum trichloride, iron(III) chloride, tin(IV) chloride, titanium(IV) chloride and zinc(II) chloride.

The halogenating agent is generally used in an equimolar amount, but it may also be used in deficiency, in excess, or, if appropriate, as the solvent. The halogenated carbamates of the formula II can be worked up and isolated in a manner known per se.

It may be advantageous to partly or fully scavenge the by-products formed in the reaction from the halogenating reagent by addition of a suitable base.

In particular, it is possible in this way to prepare para-chlorinated carbamates of the formula II.A.1
where $R^1$=chlorine and $R^b$ and $R^d$=hydrogen
by chlorinating corresponding carbamates of the formula II.A.1
where $R^a$, $R^b$ and $R^d$=hydrogen:

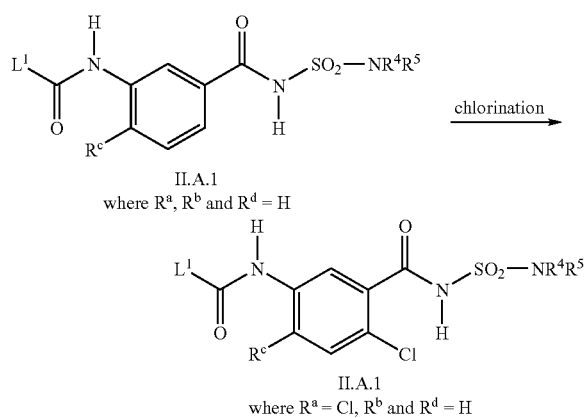

Preference is given to the chlorination especially of those carbamates of the formula II.A.1 where $R^a$, $R^b$ and $R^d$=hydrogen in which the variables $L^1$, $R^c$ and also $R^4$ and $R^5$, each alone and also in combination with one another, are defined as follows:

$L^1$ is a nucleophilically displaceable leaving group,
  preferably $C_1$-$C_6$-alkoxy or $C_1$-$C_6$-alkylthio,
  more preferably $C_1$-$C_6$-alkoxy,
  especially preferably $C_1$-$C_4$-alkoxy,
  very preferably methoxy or ethoxy;
$R^c$ is hydrogen or halogen,
  especially preferably hydrogen, fluorine or chlorine,
  very preferably hydrogen or fluorine,
  exceptionally preferably fluorine;
$R^4$ and $R^5$ are each independently
  hydrogen or $C_1$-$C_6$-alkyl which may in turn be substituted by a substituent selected from the group of halogen, cyano and $C_1$-$C_4$-alkoxy, preferably halogen;
  especially preferably
  $R^4$ is hydrogen, $C_1$-$C_6$-alkyl, $C_2$-$C_6$-alkenyl or $C_2$-$C_6$-alkynyl,
  very preferably hydrogen or $C_1$-$C_6$-alkyl,
  more preferably $C_1$-$C_4$-alkyl,
  exceptionally preferably methyl; and $R^5$ is $C_1$-$C_6$-alkyl, $C_3$-$C_8$-cycloalkyl or phenyl,
  very preferably $C_1$-$C_6$-alkyl,
  more preferably $C_1$-$C_4$-alkyl.

The reaction described here of the amines of the formula IV with compounds of the formula V affords the carbamates of the formula II in high yield.

A further preferred embodiment therefore relates to a process in which the amines of the formula IV are reacted in a first step with compounds of the formula V to give carbamates of the formula II, and the carbamates of the formula II are subsequently reacted without isolation with the enamines of the formula III to give 3-phenyl(thio)-uracils and -dithiouracils of the formula I. To this end, it may be advantageous when a portion or the entirety of the solvent used to prepare the carbamate of the formula II is removed and substituted by another solvent. However, the reaction of the carbamates of the formula II with the enamines of the formula III will in particular be carried out in the solvent used to prepare the carbamate of the formula II.

The following steps of the process according to the invention are specified as especially preferred, the preference applying both to each individual step and to the overall process. The preferred embodiments of the following steps are as specified above.

In one embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen; by reacting corresponding carbamates of the formula II.A.1 where $R^a$ is chlorine and $R^b$ and $R^d$ are each hydrogen with enamines of the formula III where $R^1$ is hydrogen; and $X^2$ is oxygen, and then alkylating the 3-phenyluracil of the formula I.A.1 thus formed, where $R^a$ is chlorine and $R^1$, $R^b$ and $R^d$ are each hydrogen with an alkylating agent of the formula VI where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $L^4$ is a nucleophilically displaceable leaving group to give 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen.

In a further embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen; by reacting corresponding carbamates of the formula II.A.1 where $R^a$ is chlorine and $R^b$ and $R^d$ are each hydrogen with enamines of the formula III where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $X^2$ is oxygen.

In a further embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen by chlorinating carbamates of the formula II.A.1 where $R^a$, $R^b$ and $R^d$=hydrogen to give para-chlorinated carbamates of the formula II.A.1 where $R^a$=chlorine and $R^b$ and $R^d$=hydrogen, then reacting them with enamines of the formula III where $R^1$ is hydrogen; and $X^2$ is oxygen, and then alkylating the 3-phenyluracil of the formula I.A.1 thus formed, where $R^a$ is chlorine and $R^1$, $R^b$ and $R^d$ are each hydrogen with an alkylating agent of the formula VI where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $L^4$ is a nucleophilically displaceable leaving group to give 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen.

In a further embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen by chlorinating carbamates of the formula II.A.1 where $R^a$, $R^b$ and $R^d$=hydrogen to give para-chlorinated carbamates of the formula II.A.1 where $R^1$=chlorine and $R^b$ and $R^d$=hydrogen, and then reacting them with enamines of the formula III where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $X^2$ is oxygen.

In a further embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen
by reacting corresponding amines of the formula IV.A.1 where $R^a$, $R^b$ and $R^d$ are each hydrogen with compounds V where $X^1$ is oxygen;
then chlorinating the carbamates of the formula II.A.1 thus obtained, where $R^a$, $R^b$ and $R^d$=hydrogen, to give para-chlorinated carbamates of the formula II.A.1 where $R^a$=chlorine and $R^b$ and $R^d$=hydrogen,
then reacting them with enamines of the formula III where $R^1$ is hydrogen; and $X^2$ is oxygen,
and then alkylating the 3-phenyluracil of the formula I.A.1 thus formed, where $R^a$ is chlorine and $R^1$, $R^b$ and $R^d$ are each hydrogen with an alkylating agent of the formula VI where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $L^4$ is a nucleophilically displaceable leaving group to give 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen.

In a further embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen
by reacting corresponding amines of the formula IV.A.1 where $R^a$=chlorine and $R^b$ and $R^d$ are each hydrogen with compounds V where $X^1$ is oxygen;
then reacting the carbamates of the formula II.A.1 thus obtained, where $R^a$=chlorine and $R^b$ and $R^d$=hydrogen, with enamines of the formula III where $R^1$ is hydrogen; and $X^2$ is oxygen,
and then alkylating the 3-phenyluracil of the formula I.A.1 thus formed, where $R^a$ is chlorine and $R^1$, $R^b$ and $R^d$ are each hydrogen, with an alkylating agent of the formula VI where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $L^4$ is a nucleophilically displaceable leaving group to give 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen.

In a further embodiment of the process according to the invention, it is possible to prepare 3-phenyluracils of the formula I.A.1 where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $R^b$ and $R^d$ are each hydrogen
by reacting corresponding amines of the formula IV.A.1 where $R^a$=chlorine and $R^b$ and $R^d$ are each hydrogen with compounds V where $X^1$ is oxygen; and then reacting the carbamates of the formula II.A.1 thus obtained, where $R^a$=chlorine and $R^b$ and $R^d$=hydrogen, with enamines of the formula III where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl, and $X^2$ is oxygen.

In a further embodiment of the process according to the invention, it is possible to prepare 3-phenyluracils of the formula I.A.1 where $R^1$, $R^b$ and $R^d$ are each hydrogen; by reacting corresponding amines of the formula IV.A.1 where $R^a$=chlorine and $R^b$ and $R^d$ are each hydrogen with compounds V where $X^1$ is oxygen; and
then reacting the carbamates of the formula II.A.1 formed, where $R^a$ is chlorine and $R^b$ and $R^d$ are each hydrogen, with enamines of the formula III where $R^1$ is hydrogen.

The process according to the invention allows for the first time the preparation of carbamates of the formula II

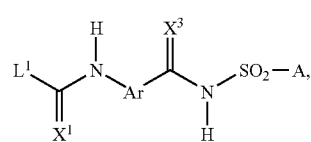

where $X^1$ and $X^3$ and also Ar and A are each as defined above and $L^1$ is a nucleophilically displaceable leaving group, preferably $C_1$-$C_6$-alkoxy or $C_1$-$C_6$-alkylthio, more preferably $C_1$-$C_6$-alkoxy.

These compounds are novel and likewise form part of the subject-matter of the present invention.

Among the carbamates of the formula II, preference is given to those of the formula II.A (=carbamates of the formula II where $X^1$ and $X^3$ are each oxygen and Ar is Ar-1)

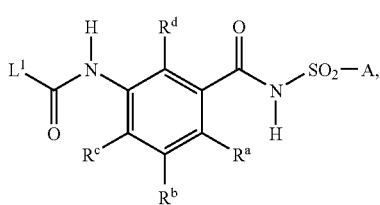

II.A where the variables $R^a$, $R^b$, $R^c$ and $R^d$ and also A and $L^1$ are each as defined above.

Very particular preference is given to the carbamates of the formula II.A.1 (=carbamates of the formula II, where $X^1$ and $X^3$ are each oxygen, Ar is Ar-1 and A is $NR^4R^5$)

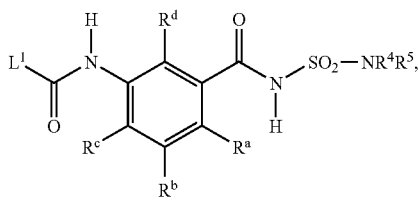

II.A.1 where the variables $R^a$, $R^b$, $R^c$ and $R^d$ and also $R^4$, $R^5$ and $L^1$ are each as defined above.

Among the carbamates of the formula II.A.1, preference is given in particular to those in which the variables $L^1$, $R^a$, $R^b$, $R^c$ and $R^d$ and also $R^4$ and $R^5$, each alone or in combination, are defined as follows:

$L^1$ nucleophilically displaceable leaving group,
  preferably $C_1$-$C_6$-alkoxy or $C_1$-$C_6$-alkylthio,
  more preferably $C_1$-$C_6$-alkoxy,
  especially preferably $C_1$-$C_4$-alkoxy,
  very preferably methoxy or ethoxy;

$R^a$ is hydrogen, halogen or cyano,
  especially preferably hydrogen, fluorine, chlorine or cyano,
  very preferably hydrogen, chlorine or cyano,
  exceptionally preferably hydrogen or chlorine;

$R^b$ hydrogen;

$R^c$ hydrogen or halogen,
  especially preferably hydrogen, fluorine, or chlorine,
  very preferably hydrogen or fluorine,
  exceptionally preferably fluorine;

$R^d$ hydrogen;

$R^4$ and $R^5$ each independently
  hydrogen or $C_1$-$C_6$-alkyl which may itself be substituted by one substituent selected from the group of halogen, cyano and $C_1$-$C_4$-alkoxy, preferably halogen;
  especially preferably
  $R^4$ hydrogen, $C_1$-$C_6$-alkyl, $C_2$-$C_6$-alkenyl or $C_2$-$C_6$-alkynyl,
    very preferably hydrogen or $C_1$-$C_6$-alkyl,
    more preferably $C_1$-$C_4$-alkyl,
    exceptionally preferably methyl; and
  $R^5$ $C_1$-$C_6$-alkyl, $C_3$-$C_8$-cycloalkyl or phenyl,
    very preferably $C_1$-$C_6$-alkyl,
    more preferably $C_1$-$C_4$-alkyl.

Exceptional preference is given to the carbamates of the formula II.A.1.a (corresponding to carbamates of the formula II where $L^1$=methoxy, $X^1$, $X^3$=oxygen, Ar=Ar-1 where $R^b$ and $R^d$=hydrogen and $R^c$=fluorine, and A=$NR^4R^5$), especially the carbamates of the formula II.A.1.a.1 to II.A.1.a.60 of Table 1, the definitions of the variables $R^a$, $R^4$ and $R^5$ play a particular role for the inventive compounds not only in combination with one another but also in each case viewed alone.

TABLE 1

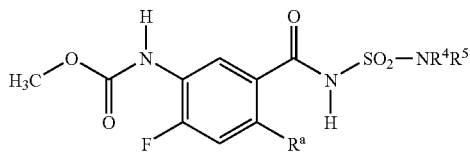

II.A.1.a

| No. | $R^a$ | $R^4$ | $R^5$ |
|---|---|---|---|
| II.A.1.a.1 | H | H | H |
| II.A.1.a.2 | H | H | $CH_3$ |
| II.A.1.a.3 | H | H | $C_2H_5$ |
| II.A.1.a.4 | H | H | $(CH_2)_2CH_3$ |
| II.A.1.a.5 | H | H | $CH(CH_3)_2$ |
| II.A.1.a.6 | H | H | $(CH_2)_3CH_3$ |
| II.A.1.a.7 | H | H | $CH(CH_3)CH_2CH_3$ |
| II.A.1.a.8 | H | H | $CH_2CH(CH_3)CH_3$ |
| II.A.1.a.9 | H | H | $C(CH_3)_3$ |
| II.A.1.a.10 | H | H | $CH_2CH=CH_2$ |
| II.A.1.a.11 | H | H | $CH_2-C\equiv CH$ |
| II.A.1.a.12 | H | $CH_3$ | $CH_3$ |
| II.A.1.a.13 | H | $CH_3$ | $C_2H_5$ |
| II.A.1.a.14 | H | $CH_3$ | $(CH_2)_2CH_3$ |
| II.A.1.a.15 | H | $CH_3$ | $CH(CH_3)_2$ |
| II.A.1.a.16 | H | $CH_3$ | $(CH_2)_3CH_3$ |
| II.A.1.a.17 | H | $CH_3$ | $CH(CH_3)CH_2CH_3$ |
| II.A.1.a.18 | H | $CH_3$ | $CH_2CH(CH_3)CH_3$ |
| II.A.1.a.19 | H | $CH_3$ | $C(CH_3)_3$ |
| II.A.1.a.20 | H | $CH_3$ | $CH_2CH=CH_2$ |
| II.A.1.a.21 | H | $CH_3$ | $CH_2-C\equiv CH$ |
| II.A.1.a.22 | H | $C_2H_5$ | $C_2H_5$ |
| II.A.1.a.23 | H | $C_2H_5$ | $(CH_2)_2CH_3$ |
| II.A.1.a.24 | H | $C_2H_5$ | $CH(CH_3)_2$ |
| II.A.1.a.25 | H | $C_2H_5$ | $(CH_2)_3CH_3$ |
| II.A.1.a.26 | H | $C_2H_5$ | $CH(CH_3)CH_2CH_3$ |
| II.A.1.a.27 | H | $C_2H_5$ | $CH_2CH(CH_3)CH_3$ |
| II.A.1.a.28 | H | $C_2H_5$ | $C(CH_3)_3$ |
| II.A.1.a.29 | H | $C_2H_5$ | $CH_2CH=CH_2$ |
| II.A.1.a.30 | H | $C_2H_5$ | $CH_2-C\equiv CH$ |
| II.A.1.a.31 | Cl | H | H |
| II.A.1.a.32 | Cl | H | $CH_3$ |
| II.A.1.a.33 | Cl | H | $C_2H_5$ |
| II.A.1.a.34 | Cl | H | $(CH_2)_2CH_3$ |
| II.A.1.a.35 | Cl | H | $CH(CH_3)_2$ |
| II.A.1.a.36 | Cl | H | $(CH_2)_3CH_3$ |
| II.A.1.a.37 | Cl | H | $CH(CH_3)CH_2CH_3$ |
| II.A.1.a.38 | Cl | H | $CH_2CH(CH_3)CH_3$ |
| II.A.1.a.39 | Cl | H | $C(CH_3)_3$ |
| II.A.1.a.40 | Cl | H | $CH_2CH=CH_2$ |
| II.A.1.a.41 | Cl | H | $CH_2-C\equiv CH$ |
| II.A.1.a.42 | Cl | $CH_3$ | $CH_3$ |
| II.A.1.a.43 | Cl | $CH_3$ | $C_2H_5$ |
| II.A.1.a.44 | Cl | $CH_3$ | $(CH_2)_2CH_3$ |
| II.A.1.a.45 | Cl | $CH_3$ | $CH(CH_3)_2$ |
| II.A.1.a.46 | Cl | $CH_3$ | $(CH_2)_3CH_3$ |
| II.A.1.a.47 | Cl | $CH_3$ | $CH(CH_3)CH_2CH_3$ |
| II.A.1.a.48 | Cl | $CH_3$ | $CH_2CH(CH_3)CH_3$ |
| II.A.1.a.49 | Cl | $CH_3$ | $C(CH_3)_3$ |
| II.A.1.a.50 | Cl | $CH_3$ | $CH_2CH=CH_2$ |
| II.A.1.a.51 | Cl | $CH_3$ | $CH_2-C\equiv CH$ |
| II.A.1.a.52 | Cl | $C_2H_5$ | $C_2H_5$ |
| II.A.1.a.53 | Cl | $C_2H_5$ | $(CH_2)_2CH_3$ |
| II.A.1.a.54 | Cl | $C_2H_5$ | $CH(CH_3)_2$ |
| II.A.1.a.55 | Cl | $C_2H_5$ | $(CH_2)_3CH_3$ |

TABLE 1-continued

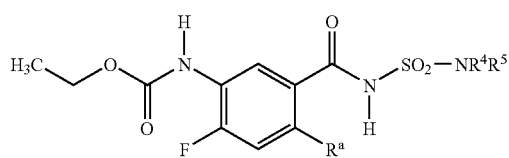

II.A.1.a

| No. | $R^a$ | $R^4$ | $R^5$ |
|---|---|---|---|
| II.A.1.a.56 | Cl | $C_2H_5$ | $CH(CH_3)CH_2CH_3$ |
| II.A.1.a.57 | Cl | $C_2H_5$ | $CH_2CH(CH_3)CH_3$ |
| II.A.1.a.58 | Cl | $C_2H_5$ | $C(CH_3)_3$ |
| II.A.1.a.59 | Cl | $C_2H_5$ | $CH_2CH{=}CH_2$ |
| II.A.1.a.60 | Cl | $C_2H_5$ | $CH_2{-}C{\equiv}CH$ |

Equally exceptionally preferred are the carbamates of the formula II.A.1.b, especially the compounds of the formula II.A.1.b.1 to II.A.1.b.60 which differ from the corresponding compounds of the formula II.A.1.a.1 to II.A.1.a.60 in that $L^1$ is ethoxy.

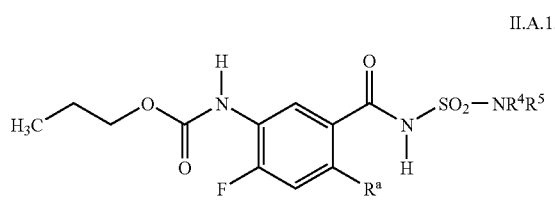

II.A.1.b

Equally exceptionally preferred are the carbamates of the formula II.A.1.c, especially the compounds of the formula II.A.1.c.1 to II.A.1.c.60 which differ from the corresponding compounds of the formula II.A.1.a.1 to II.A.1.a.60 in that $L^1$ is n-propyloxy.

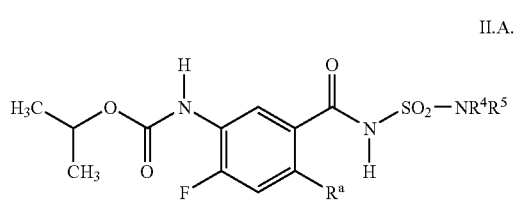

II.A.1.c

Equally exceptionally preferred are the carbamates of the formula II.A.1.d, especially the compounds of the formula II.A.1.d.1 to II.A.1.d.60 which differ from the corresponding compounds of the formula II.A.1.a.1 to II.A.1.a.60 in that $L^1$ is isopropyloxy.

II.A.1.d

Equally exceptionally preferred are the carbamates of the formula II.A.1.e, especially the compounds of the formula II.A.1.e.1 to II.A.1.e.60 which differ from the corresponding compounds of the formula II.A.1.a.1 to II.A.1.a.60 in that $L^1$ is sec-butyloxy.

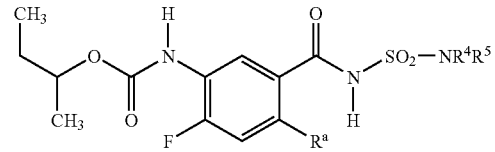

II.A.1.e

Equally exceptionally preferred are the carbamates of the formula II.A.1.f, especially the compounds of the formula II.A.1.f.1 to II.A.1.f.60 which differ from the corresponding compounds of the formula II.A.1.a.1 to II.A.1.a.60 in that $L^1$ is isobutyloxy.

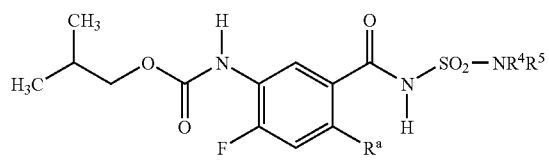

II.A.1.f

Equally exceptionally preferred are the carbamates of the formula II.A.1.g, especially the compounds of the formula II.A.1.g.1 to II.A.1.g.60 which differ from the corresponding compounds of the formula II.A.1.a.1 to II.A.1.a.60 in that $L^1$ is tert-butyloxy.

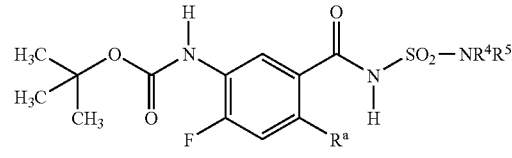

II.A.1.g

Equally exceptionally preferred are the carbamates of the formula II.A.1.h, especially the compounds of the formula II.A.1.h.1 to II.A.1.h.60 which differ from the corresponding compounds of the formula II.A.1.a.1 to II.A.1.a.60 in that $L^1$ is methylthio.

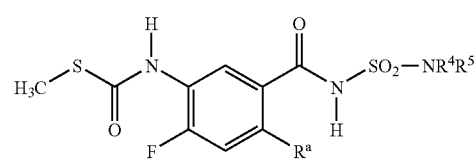

II.A.1.h

Equally exceptionally preferred are the carbamates of the formula II.A.1.i, especially the compounds of the formula II.A.1.i.1 to II.A.1.i.60 which differ from the corresponding compounds of the formula II.A.1.a.1 to II.A.1.a.60 in that $L^1$ is ethylthio.

II.A.1.i

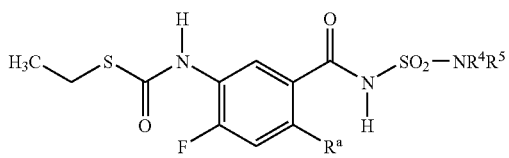

SYNTHESIS EXAMPLES

The examples which follow serve to illustrate the invention.

1. Preparation of the Carbamates of the Formula II

Example 1.1

N-{4-Fluoro-3-[(ethoxycarbonyl)amino]benzoyl}-N'-isopropyl-N'-methylsulfamide

Compound II.A.1.b.15

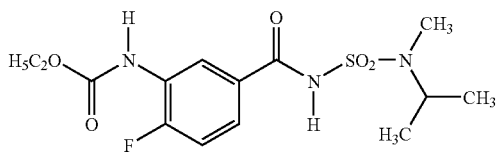

Example 1.1.a 14.13 g (0.179 mol) of pyridine were added dropwise at room temperature to a solution of 41.0 g (0.138 mol) of N-(4-fluoro-3-aminobenzoyl)-N'-isopropyl-N'-methylsulfamide in methylene chloride and the mixture was subsequently cooled to 0-5° C. At this temperature, 19.83 g (0.183 mol) of ethyl chloroformate in methylene chloride were added in portions and the mixture was subsequently stirred for 60 min. The reaction mixture was hydrolyzed and the removed organic phase was extracted with $H_2O$ and 10% hydrochloric acid. Subsequently, the organic phase was washed and dried, and the solvent was removed.

47.9 g (96% of theory) of the title compound were obtained (m.p.: 142-144° C.)

$^1$H NMR (500 MHz, d-DMSO) δ[ppm]=11.9 (s, 1H), 9.50 (s, 1H), 8.30 (d, 1H), 7.65-7.70 (m, 1H), 7.35 (t, 1H), 4.10-4.25 (m, 3H), 2.90 (s, 3H), 1.28 (t, 3H), 1.10 (d, 6H).

Analogously to Example 1.1.a, the following examples 1.1.b to 1.1.e were carried out:

Example 1.1.b 6.10 g (0.020 mol) of N-(4-fluoro-3-aminobenzoyl)-N'-isopropyl-N'-methylsulfamide
3.87 g (0.041 mol) of picoline
2.97 g (0.027 mol) of ethyl chloroformate
6.1 g (95% of theory) of the title compound were obtained.

Example 1.1.c 6.00 g (0.020 mol) of N-(4-fluoro-3-aminobenzoyl)-N'-isopropyl-N'-methylsulfamide
2.47 g (0.062 mol) of NaOH
2.97 g (0.027 mol) of ethyl chloroformate
6.4 g (95% of theory) of the title compound were obtained.

Example 1.1.d 6.00 g (0.020 mol) of N-(4-fluoro-3-aminobenzoyl)-N'-isopropyl-N'-methylsulfamide
3.72 g (0.027 mol) of $K_2CO_3$
3.00 g (0.027 mol) of ethyl chloroformate
6.0 g (76% of theory) of the title compound were obtained.

Example 1.1.e 5.90 g (0.020 mol) of N-(4-fluoro-3-aminobenzoyl)-N'-isopropyl-N'-methylsulfamide
2.47 g (0.062 mol) of triethylamine
0.24 g (0.062 mol) of dimethylaminopyridine (DMAP)
2.89 g (0.027 mol) of ethyl chloroformate
6.1 g (52% of theory) of the title compound were obtained.

Example 1.1.f 134.7 g (1.22 mol) of ethyl chloroformate were added in portions at 115-125° C. to a solution of 300.0 g (0.897 mol) of N-(4-fluoro-3-aminobenzoyl)-N'-isopropyl-N'-methylsulfamide in chlorobenzene and the mixture was subsequently stirred at 125° C. for 2 h. Afterward, the solvent and the excess ethyl chloroformate were removed. 312.8 g (96% of theory) of the title compound were obtained.

Example 1.2

N-{6-Chloro-4-fluoro-3-[(ethoxycarbonyl)amino]benzoyl}-N'-isopropyl-N'-methylsulfamide Compound II.A.1.b.45

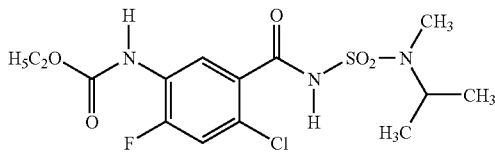

57.7 g (0.729 mol) of pyridine were added dropwise at room temperature to a solution of 200.0 g (0.565 mol) of N-(6-chloro-4-fluoro-3-aminobenzoyl)-N'-isopropyl-N'-methylsulfamide in methylene chloride and the mixture was subsequently cooled to 0-5° C. Subsequently, 80.99 g (0.746 mol) of ethyl chloroformate in methylene chloride were added in portions and the mixture was left to stir for 60 min. The reaction mixture was then hydrolyzed and the removed organic phase was extracted with $H_2O$ and 10% hydrochloric acid. Subsequently, the organic phase was washed and dried, and the solvent was removed.

156.4 g (86% of theory) of the title compound were obtained.

$^1$H NMR (400 MHz, $CDCl_3$): δ=8.70 (s, 1H), 8.45 (d, 1H), 7.20 (d, 1H), 6.90 (s, 1H) 4.20-4.40 μm, 3H), 3.00 (s, 3H), 1.35 (t, 3H), 1.20 (d, 6H).

Example 1.3

N-{4-Fluoro-3-[(methoxycarbonyl)amino]benzoyl}-N'-isopropyl-N'-methylsulfamide

Compound II.A.1.a.15

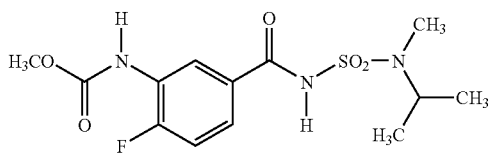

5.52 g (0.057 mol) of methyl chloroformate were added in portions at 115-125° C. to a solution of 12.50 g (0.042 mol) of N-(4-fluoro-3-aminobenzoyl)-N'-isopropyl-N'-methylsulfamide in chlorobenzene, and the mixture was then stirred at 125° C. for 2 h. The solvent and the excess methyl chloroformate were then removed.

14.9 g (99% of theory) of the title compound were obtained.

$^1$H NMR (500 MHz, CDCl$_3$): δ=9.25 (s, 1H), 8.55 (d, 1H), 7.55-7.60 (m, 1H), 7.15 (t, 1H), 6.95 (s, 1H) 4.20-4.30 (m, 1H), 3.00 (s, 3H), 2.95 (s, 3H), 1.18 ppm (d, 6H).

Example 1.4

N-{4-Fluoro-3-[(phenoxycarbonyl)amino]benzoyl}-N'-isopropyl-N'-methylsulfamide

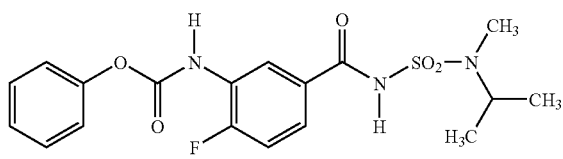

6.69 g (0.057 mol) of phenyl chloroformate were added in portions at 115-125° C. to a solution of 12.50 g (0.042 mol) of N-(4-fluoro-3-aminobenzoyl)-N'-isopropyl-N'-methylsulfamide in chlorobenzene, and the mixture was then stirred at 125° C. for 2 h. The solvent and the excess phenyl chloroformate were then removed.

17.7 g (98% of theory) of the title compound were obtained.

$^1$H NMR (500 MHz, CDCl$_3$): δ=9.05 (s, 1H), 7.55-7.60 (m, 1H), 7.25-7.40 (m, 7H), 4.20-4.30 (m, 1H), 3.00 (s, 3H), 1.20 ppm (d, 6H).

Example 1.5

N-{4-Fluoro-3-[(n-butyloxycarbonyl)amino]benzoyl}-N'-isopropyl-N'-methylsulfamide

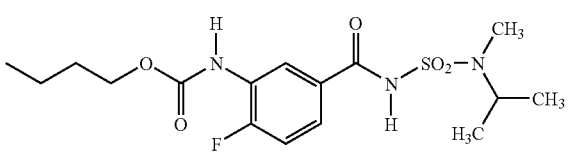

7.36 g (0.053 mol) of n-butyl chloroformate were added in portions at 115-125° C. to a solution of 12.50 g (0.042 mol) of N-(4-fluoro-3-aminobenzoyl)-N'-isopropyl-N'-methylsulfamide in chlorobenzene, and the mixture was then stirred at 125° C. for 2 h. The solvent and the excess n-butyl chloroformate were then removed.

18.0 g (93% of theory) of the title compound were obtained.

$^1$H NMR (500 MHz, CDCl$_3$): δ=9.15 (s, 1H), 8.55 (d, 1H), 7.55-7.60 (m, 1H), 7.15 (t, 1H), 6.95 (s, 1H), 4.20-4.35 (m, 3H), 3.00 (s, 3H), 2.95 (s, 3H), 1.60 (q, 2H), 1.35 (q, 2H), 1.18 ppm (6H), 0.95 (t, 3H).

Example 1.6

N-{4-Fluoro-3-[(isopropyloxycarbonyl)amino]benzoyl}-N'-isopropyl-N'-methylsulfamide Compound II.A.1.d.15

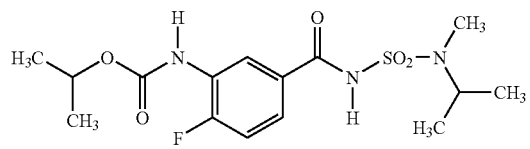

83 g of a 1 M solution of isopropyl chloroformate in toluene (corresponds to 0.097 mol of isopropyl chloroformate) were added in portions at 115-125° C. to a solution of 12.50 g (0.042 mol) of N-(4-fluoro-3-aminobenzoyl)-N'-isopropyl-N'-methylsulfamide in toluene, and then the mixture was stirred at 125° C. for 2 h. The solvent and the excess isopropyl chloroformate were then removed.

16.1 g (97% of theory) of the title compound were obtained.

$^1$H NMR (500 MHz, CDCl$_3$): δ=9.10 (s, 1H), 8.55 (d, 1H), 7.55-7.60 (m, 1H), 7.10 (t, 1H), 6.90 (s, 1H) 4.95-5.10 (m, 1H), 4.20-4.30 (m, 1H), 2.95 (s, 3H), 1.35 (d, 6H), 1.18 ppm (d, 6H).

2. Preparation of the Chlorinated Carbamates of the Formula II

Example 2.1

N-{2-Chloro-4-fluoro-5-[(ethoxycarbonyl)amino]benzoyl}-N'-isopropyl-N'-methylsulfamide Compound II.A.1.b.45

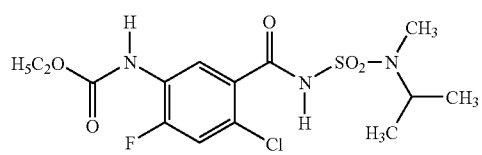

Example 2.1.a 150 g (0.407 mol) of N-(3-[(ethoxycarbonyl)amino]-4-fluorobenzoyl)-N'-isopropyl-N'-methylsulfamide suspended in chlorobenzene were concentrated in a reaction vessel under reduced pressure (internal temperature <100° C.).

Afterward, the vacuum was broken and the suspension cooled to 65° C. Subsequently, 760 g (5.517 mol) of sulfuryl chloride were added in portions, in the course of which the temperature was kept at 50° C. Subsequently, the mixture was stirred for a further 16 h.

Excess sulfuryl chloride was then removed by distillation. The distillation residue was admixed with chlorobenzene and water and cooled to room temperature, and the pH of the thus obtained suspension was adjusted to pH=5 using 2N sodium hydroxide solution. Subsequently, the product was filtered off, washed and dried. 126.5 g (75% of theory) of the title compound were obtained (m.p.: 98-100° C.).

Example 2.1.b 40 g (0.11 mol) of N-{3-[(ethoxycarbonyl)amino]-4-fluorobenzoyl}-N'-isopropyl-N'-methylsulfamide were added to 179.3 g (1.33 mol) of sulfuryl chloride and stirred at 40° C. for 10 h. Excess sulfuryl chloride and chlorobenzene were subsequently removed by distillation. The residue was admixed at 75° C. with stirring initially with toluene, then with water. At 80-85° C., the pH was adjusted to pH=4 by means of 2N sodium hydroxide solution and the mixture was cooled to 20° C. with stirring. The precipitated product was filtered off, washed and dried.

33 g (71% of theory) of the title compound were obtained (m.p.: 98-100° C.).

Example 2.2

N-{2-Chloro-4-fluoro-5-[(methoxycarbonyl)amino]benzoyl}-N'-isopropyl-N'-methylsulfamide Compound II.A.1.b.45

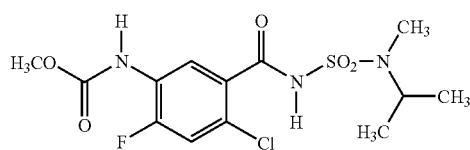

40 g (0.112 mol) of N-(3-[(methoxycarbonyl)amino]-4-fluorobenzoyl}-N'-isopropyl-N'-methylsulfamide suspended in chlorobenzene were concentrated in a reaction vessel under reduced pressure. The vacuum was then broken and the suspension was cooled to 65° C. Subsequently, 197 g (1.430 mol) of sulfuryl chloride were added in portions, in the course of which the temperature was kept at 50° C. Subsequently, the mixture was stirred for a further 16 h.

Excess sulfuryl chloride was then removed by distillation. The distillation residue was admixed with chlorobenzene and water, and cooled to room temperature, and the pH of the suspension thus obtained was adjusted to pH=5 with 2N sodium hydroxide solution. The product was then filtered off, washed and dried.

14.6 g (34% of theory) of the title compound were obtained.

$^1$H NMR (500 MHz, d-DMSO): δ=11.1 (s, 1H), 9.80 (s, 1H), 7.90-7.95 (m, 1H), 7.60-7.70 (m, 1H), 4.25-4.30 (m, 1H), 3.80 (s, 3H), 2.85 (s, 3H), 1.15 (d, 6H).

3. Preparation of the Phenyl(thio)uracils and -Dithiouracils of the Formula I

Example 3.1

2-Chloro-5-[3,6-dihydro-2,6-dioxo-4-(trifluoromethyl)-1(2H)-pyrimidinyl]-4-fluoro-N-{[methyl(1-methylethyl)amino]sulfonyl}benzamide

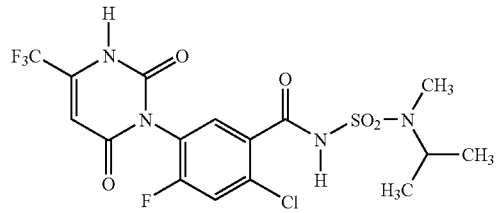

Example 3.1.a 9.13 g (0.049 mol) of ethyl 3-amino-4,4,4-trifluoro-2-butenoate were initially charged in DMF at room temperature. 12.84 g (0.059 mol) of potassium methoxide solution (32% in methanol) were added and the mixture was left to stir for a further 30 min. Subsequently, 20 g (0.049 mol) of N-(2-chloro-4-fluoro-5-[(ethoxycarbonyl)amino]-benzoyl)-N'-isopropyl-N'-methylsulfamide were added. The reaction mixture was heated and sufficient alcohol was distilled off to attain 119° C. While distilling off alcohol, 11.75 g (0.054 mol) of potassium methoxide solution (32% in methanol) were then added in portions within a few hours. For the work up, the reaction mixture was added dropwise with cooling to dilute hydrochloric acid, and the pH at the end was <2. The precipitated product was filtered off, washed and dried.

22.5 g (92.7% of theory) of the title compound were obtained [m.p. 238° C. (decomposition)].

Example 3.1.b 1.2 g (6.8 mmol) of ethyl 3-amino-4,4,4-trifluoro-2-butenoate were initially charged in DMF at room temperature. 1.9 g (13.7 mmol) of potassium carbonate were added and the mixture was left to stir at 50° C. for 1 h. Subsequently, 2.4 g (5.7 mmol) of N-(2-chloro-4-fluoro-5-[(ethoxycarbonyl)amino]benzoyl)-N'-isopropyl-N'-methylsulfamide were added, the temperature was increased to 120° C. and the mixture was stirred for a further 4.5 h. For the work up, the reaction mixture was added dropwise with cooling to dilute hydrochloric acid, and the pH at the end of the reaction was <2. The precipitated product was filtered off, washed and dried.

2.3 g (73% of theory) of the title compound were obtained.

Example 3.2

2-Chloro-5-[3,6-dihydro-3-methyl-2,6-dioxo-4-(trifluoromethyl)-1(2H)-Pyrimidinyl]-4-fluoro-N-[[methyl-(1-methylethyl)amino]sulfonyl]benzamide

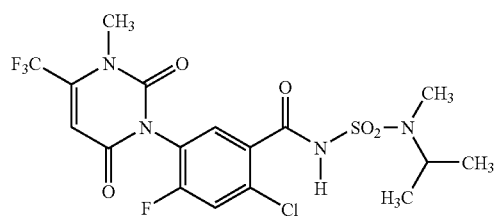

1.14 g (9.04 mmol) of dimethyl sulfate and 0.283 g (2.055 mmol) of K$_2$CO$_3$ were added to 2.0 g (4.11 mmol) of 2-chloro-5-[3,6-dihydro-2,6-dioxo-4-(trifluoromethyl)-1(2H)pyrimidinyl]-4-fluoro-N-[[methyl(1-methylethyl)amino]sulfonyl]benzamide from example 1 in 80 ml of N,N-dimethylformamide, and the mixture was then stirred at 25° C. for 16 hours. Subsequently, the N,N-dimethylformamide was distilled off at 30° C. and reduced pressure and the residue was taken up in about 250 ml of ethyl acetate. The reaction mixture was acidified with 10% HCl and then extracted twice with water. The organic phase was dried over MgSO$_4$ and the solvent was distilled off to obtain 1.95 g of the crude product. According to $^1$H NMR and HPLC, the purity of the product of value was 77% (corresponds to a yield of 73%). For purification, 0.92 g of this crude product was chromatographed on silica gel (28×4.5 cm column) with from 9/1 to 1/1 cyclohexane/ethyl acetate to obtain four fractions. The 3rd fraction (0.58 g; corresponds to 59% isolated yield) comprised the desired product of value in pure form.

$^1$H NMR data (DMSO-d$_6$) δ (ppm): 12.2 (NH), 7.8 (d, 1H), 7.7 (d, 1H), 6.6 (s, 1H), 4.1 (sept, 1H), 3.5 (s, 3H), 3.3 (s, 3H), 2.9 (s, 3H), 1.2 (d, 6H)

Example 3.3

2-Chloro-5-[3,6-dihydro-3-methyl-2,6-dioxo-4-(trifluoromethyl)-1(2H)-pyrimidinyl]-4-fluoro-N-[[methyl-(1-methylethyl)amino]sulfonyl]benzamide

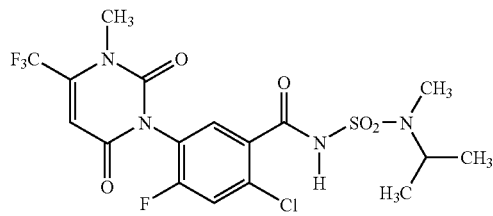

12.45 g (0.024 mol) of 2-chloro-5-[3,6-dihydro-2,6-dioxo-4-(trifluoromethyl)-1(2H)pyrimidinyl]-4-fluoro-N-[[methyl(1-methylethyl)amino]sulfonyl]benzamide (93.9% pure) from example 1 were added at 25° C. to a solvent mixture of 135 g of toluene and 27 g of tetrahydrofuran, and then the mixture was admixed with a solution of 2.3 g (0.0288 mol) of sodium hydroxide (50%) in 57.5 g of water. 0.77 g (0.0024 mol) of tetrabutylammonium bromide and 3.69 g (0.0293 mol) of dimethyl sulfate were added to the reaction mixture. The biphasic reaction mixture was stirred intensively at 25° C. for 23 hours.

The aqueous phase was then removed and the organic phase was washed twice with 100 ml each time of water. After the combined organic phase had been dried, the solvent was distilled off under reduced pressure to obtain 13.8 g of a crude product which, by quantitative HPLC, comprised the title compound to an extent of 77.5% (corresponds to a yield of 88.9%).

Example 3.4

2-Chloro-5-[3,6-dihydro-3-methyl-2,6-dioxo-4-(trifluoromethyl)-1(2H)-pyrimidinyl]-4-fluoro-N-[[methyl-(1-methylethyl)amino]sulfonyl]benzamide

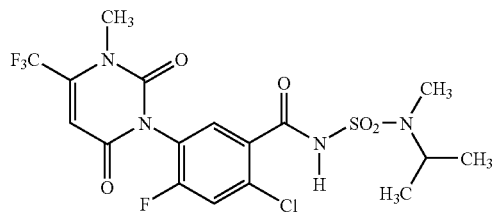

5 g (10.3 mmol) of 2-chloro-5-[3,6-dihydro-2,6-dioxo-4-(trifluoromethyl)-1(2H)pyrimidinyl-4-fluoro-N-[[methyl(1-methylethyl)amino]sulfonyl]benzamide from example 1 were added to a solvent mixture of 250 ml of dichloromethane and 125 ml of tetrahydrofuran and then admixed with a solution of 0.411 g (10.3 mmol) of NaOH in 375 ml of water. 0.38 g (1.03 mmol) of tetrabutylammonium iodide and 1.36 g (10.8 mmol) of dimethyl sulfate were added to the reaction mixture and the biphasic mixture was stirred at 1000 revolutions/min for 14 hours.

The aqueous phase was removed and the organic phase was concentrated to dryness under reduced pressure. The chromatographic purification on silica gel was effected in the manner described in example 5 to obtain 4 fractions. After the solvent had been removed, the first fraction comprised 0.54 g of a mixture which, according to $^1$H NMR, consisted of the desired product of value to an extent of 90%, and the second fraction 2 comprised 2.4 g of the product of value having a purity of >95% (yield based on the two fractions: 56%).

What is claimed is:

1. A process for preparing a 3-phenyl(thio)uracil or -dithiouracil of the formula I

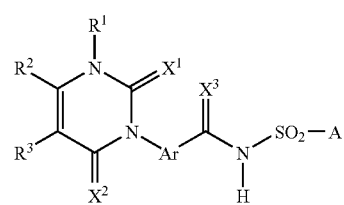

where the variables are each defined as follows:

R$^1$ is hydrogen, C$_1$-C$_6$-alkyl, C$_1$-C$_4$-cyanoalkyl, C$_1$-C$_6$-haloalkyl, C$_3$-C$_8$-cycloalkyl, C$_2$-C$_6$-alkenyl, C$_2$-C$_6$-haloalkenyl, C$_3$-C$_6$-alkynyl, C$_3$-C$_6$-haloalkynyl, phenyl-C$_1$-C$_4$-alkyl or amino, R$^2$ and R$^3$ are each independently hydrogen, C$_1$-C$_6$-alkyl, C$_1$-C$_6$-haloalkyl, C$_3$-C$_8$-cycloalkyl, C$_2$-C$_6$-alkenyl, C$_2$-C$_6$-haloalkenyl, C$_3$-C$_6$-alkynyl or C$_3$-C$_6$-haloalkynyl;

X$^1$, X$^2$ and X$^3$ are each independently oxygen or sulfur;

Ar is phenyl which may be partly or fully halogenated and/or may carry from one to three radicals selected from the group consisting of cyano, C$_1$-C$_4$-alkyl and C$_1$-C$_4$-haloalkyl, and A is NR$^4$R$^5$ where R$^4$ and R$^5$ are each independently hydrogen or C$_1$-C$_6$-alkyl;

which process comprises reacting a carbamate of the formula II

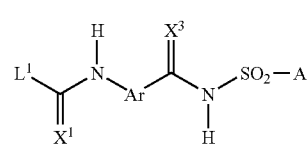

where the variables $X^1$, $X^3$, Ar and A are each as defined above and $L^1$ is $C_1$-$C_6$-alkoxy or $C_1$-$C_6$-alkylthio with an enamine of the formula III

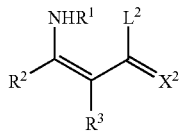
III where the variables $X^2$, $R^1$, $R^2$ and $R^3$ are each as defined above and $L^2$ is selected from the group consisting of $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2C_4$-alkoxy, $C_2$-$C_6$-alkenyloxy, $C_2$-$C_6$-haloalkenyl-oxy, $C_3$-$C_6$-alkynyloxy, $C_3$-$C_6$-haloalkynyloxy, $C_3$-$C_8$-cycloalkyloxy, $C_1$-$C_6$-cyanoalkoxy and benzyloxy
which in turn may be partially or fully halogenated on the phenyl ring and/or may be substituted by from one to three radicals selected from the group consisting of cyano, nitro, $C_1$-$C_4$-alkyl, $C_1$-$C_4$-alkoxy and $C_1$-$C_4$-alkylthio;
in the presence of an excess of base, based on the amount of the carbamate of the formula II.

2. The process according to claim 1, wherein $R^1$ is hydrogen or $C_1$-$C_4$-alkyl.

3. The process according to claim 1, wherein $R^2$ is hydrogen, $C_1$-$C_4$-alkyl or $C_1$-$C_4$-haloalkyl.

4. The process according to claim 1, wherein $R^3$ is hydrogen or $C_1$-$C_4$-alkyl.

5. The process according to claim 1, wherein $X^1$, $X^2$ and $X^3$ are each oxygen.

6. The process according to claim 1, wherein Ar is a group of the general formula Ar-1

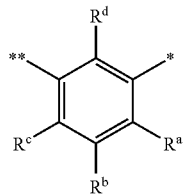
Ar-1 where
* represents the bond of Ar to the $C(X^3)$ group;
** represents the bond of Ar to the directly adjacent nitrogen atom;
$R^a$ and $R^c$ are each independently
hydrogen, halogen, cyano or $C_1$-$C_4$-haloalkyl; and
$R^b$ and $R^d$ are each hydrogen.

7. The process according to claim 1, wherein A is an —$NR^4R^5$ group where the substituents $R^4$ and $R^5$ are each independently selected from the group consisting of hydrogen and $C_1$-$C_6$-alkyl which may itself be substituted by a substituent selected from the group consisting of halogen, cyano, $C_3$-$C_8$-cycloalkyl, $C_1$-$C_4$-alkoxy, $C_1$-$C_4$-alkylthio, $C_1$-$C_4$-alkoxycarbonyl, phenyl which may itself carry from one to three radicals selected from the group consisting of halogen and $C_1$-$C_4$-alkoxy; furyl, thienyl and 1,3-dioxolanyl.

8. The process according to claim 1, wherein the carbamate of the formula II is prepared by reacting an amine of the formula IV

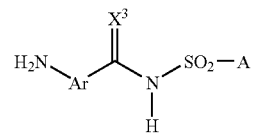
IV where $X^3$, Ar and A are each as defined in claim 1
with a compound of the formula V

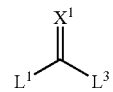
V where $X^1$ and $L^1$ are each as defined in claim 1 and
$L^3$ is chlorine or $C_1$-$C_6$-alkoxy.

9. The process according to claim 1, wherein the carbamate of the formula II is halogenated on the Ar radical with a halogenating agent in an intermediate step.

10. A carbamate of the formula II

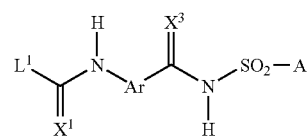
II where $X^1$ and $X^3$ are each independently oxygen or sulfur;
Ar is phenyl which may be partly or fully halogenated and/or may carry from one to three radicals selected from the group consisting of cyano, $C_1$-$C_4$-alkyl and $C_1$-$C_4$-haloalkyl,
A is $NR^4R^5$ where $R^4$ and $R^5$ are each independently hydrogen or $C_1$-$C_6$-alkyl;
$L^1$ is $C_1$-$C_6$-alkoxy or $C_1$-$C_6$-alkylthio.

11. The process for preparing a 3-phenyl(thio)uracil or -dithiouracil of the formula I according to claim 1
wherein in said 3-phenyl(thio)uracil or -dithiouracil of the formula I, $R^1$ is selected from the group consisting of $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl, phenyl-$C_1$-$C_4$-alkyl and amino;
and in said enamine of the formula III

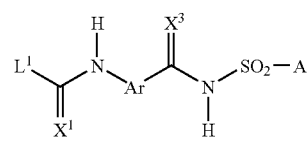
II $R^1$ is hydrogen, and $L^2$ is selected from the group consisting of $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2$-$C_4$-alkoxy, $C_2$-$C_6$-alkenyloxy, $C_2$-$C_6$-haloalkenyl-oxy, $C_3$-$C_6$-alkynyloxy, $C_3$-$C_6$-haloalkynyloxy, $C_3$-$C_8$-cycloalkyloxy, $C_1$-$C_6$-cyanoalkoxy and benzyloxy;

further comprising reacting the resulting 3-phenyl(thio) uracil or -dithiouracil of the formula I
with an alkylating agent of the formula VI $$R^1\text{-}L^4 \qquad \text{VI}$$

where $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $L^4$ is halogen, hydrogensulfate, $C_1$-$C_6$-alkylsulfate, sulfate, $C_1$-$C_6$-alkylsulfonyloxy, $C_1$-$C_6$-haloalkylsulfonyloxy or phenylsulfonyloxy where the phenyl ring is optionally mono- or polysubstituted by halogen, nitro, $C_1$-$C_6$-alkyl or $C_1$-$C_6$-haloalkyl;

to give a 3-phenyl(thio) uracil or -dithiouracil of the formula I where $R^1$ is $C_1$-$C_6$-alkyl, $C_1$-$C_4$-cyanoalkyl, $C_1$-$C_6$-haloalkyl, $C_3$-$C_8$cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl;

or with an aminating agent of the formula VII $$H_2N\text{-}L^5 \qquad \text{VII}$$

where $L^5$ is halogen, hydrogensulfate, $C_1$-$C_6$-alkylsulfonyloxy, $C_1$-$C_6$-haloalkylsulfonyloxy, phenylsulfonyloxy or phenyloxy, where the phenyl ring is optionally mono- or polysubstituted by halogen, nitro, $C_1$-$C_6$-alkyl or $C_1$-$C_6$-haloalkyl to give a 3-phenyl(thio)uracil or -dithiouracils of the formula I where $R^1$ is $NH_2$.

12. A process according to claim 11 where $R^1$ is $C_1$-$C_6$-alkyl or amino.

13. A process according to claim 11 where $R^1$ is $C_1$-$C_6$-alkyl.

14. The process according to claim 6, wherein $R^a$ is hydrogen, halogen or cyano; and $R^c$ is hydrogen or halogen.

15. The process for preparing a 3-phenyl(thio)uracil or -dithiouracil of the formula I according to claim 1 wherein in said enamine of the formula III

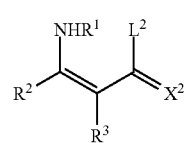

$R^1$ is hydrogen, and $L^2$ is selected from the group consisting of $C_1$-$C_6$-alkoxy, $C_1$-$C_6$-haloalkoxy, $C_1$-$C_4$-alkoxy-$C_2$-$C_4$-alkoxy, $C_1$-$C_4$-alkylthio-$C_2C_4$-alkoxy, $C_2$-$C_6$-alkenyloxy, $C_2$-$C_6$-haloalkenyl-oxy, $C_3$-$C_6$-alkynyloxy, $C_3$-$C_6$-haloalkynyloxy, $C_3$-$C_8$-cycloalkyloxy, $C_1$-$C_6$-cyanoalkoxy and benzyloxy;

further comprising reacting the resulting 3-phenyl(thio) uracil or -dithiouracil of the formula I a) with an alkylating agent of the formula VI $$R^1\text{-}L^4 \qquad \text{VI}$$

where $R^1$ in said formula VI is selected from the group consisting of $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl; and $L^4$ is selected from the group consisting of halogen, hydrogensulfate, $C_1$-$C_6$-alkylsulfate, sulfate, $C_1$-$C_6$-alkylsulfonyloxy, $C_1$-$C_6$-haloalkylsulfonyloxy and phenylsulfonyloxy, where the phenyl ring is unsubstituted or mono- or polysubstituted by halogen, nitro, $C_1$-$C_6$-alkyl or $C_1$-$C_6$-haloalkyl, to give a 3-phenyl(thio) uracil or -dithiouracil of the formula I, wherein $R^1$ is $C_1$-$C_6$-alkyl, $C_1$-$C_4$-cyanoalkyl, $C_1$-$C_6$-haloalkyl, $C_3$-$C_8$-cycloalkyl, $C_2$-$C_6$-alkenyl, $C_2$-$C_6$-haloalkenyl, $C_3$-$C_6$-alkynyl, $C_3$-$C_6$-haloalkynyl or phenyl-$C_1$-$C_4$-alkyl;

or b) with an aminating agent of the formula VII $$H_2N\text{-}L^5 \qquad \text{VII}$$

where $L^5$ is halogen, hydrogensulfate, $C_1$-$C_6$-alkylsulfonyloxy, $C_1$-$C_6$-haloalkylsulfonyloxy, phenylsulfonyloxy or phenyloxy, where the phenyl ring is unsubstituted or mono- or polysubstituted by halogen, nitro, $C_1$-$C_6$-alkyl or $C_1$-$C_6$-haloalkyl to give a 3-phenyl(thio)uracil or -dithiouracils of the formula I where $R^1$ is $NH_2$.

* * * * *